United States Patent
Grandeury et al.

(10) Patent No.: US 12,390,468 B2
(45) Date of Patent: Aug. 19, 2025

(54) CRYSTALLINE FORMS OF A SUCCINATE SALT OF 7-CYCLOPENTYL-2-(5-PIPERAZIN-1-YL-PYRIDIN-2-YLAMINO)-7H-PYRROLO[2,3-D]PYRIMIDINE-6-CARBOXYLIC ACID DIMETHYLAMIDE

(71) Applicant: Novartis AG, Basel (CH)

(72) Inventors: Arnaud Grandeury, Helfrantzkirch (FR); Nilesh Patel, Gujarat (IN); Frank Schaefer, Basel (CH); Daniel Zimmermann, Basel (CH)

(73) Assignee: Novartis AG, Basel (CH)

( * ) Notice: Subject to any disclaimer, the term of this patent is extended or adjusted under 35 U.S.C. 154(b) by 955 days.

(21) Appl. No.: 17/424,690

(22) PCT Filed: Jan. 23, 2020

(86) PCT No.: PCT/IB2020/050544
§ 371 (c)(1),
(2) Date: Jul. 21, 2021

(87) PCT Pub. No.: WO2020/152629
PCT Pub. Date: Jul. 30, 2020

(65) Prior Publication Data
US 2023/0042479 A1    Feb. 9, 2023

Related U.S. Application Data

(60) Provisional application No. 62/795,799, filed on Jan. 23, 2019.

(51) Int. Cl.
| | | |
|---|---|---|
| A61K 31/519 | (2006.01) | |
| A61K 45/06 | (2006.01) | |
| A61P 35/00 | (2006.01) | |
| C07D 487/04 | (2006.01) | |

(52) U.S. Cl.
CPC ............ *A61K 31/519* (2013.01); *A61K 45/06* (2013.01); *C07D 487/04* (2013.01); *A61P 35/00* (2018.01); *C07B 2200/13* (2013.01)

(58) Field of Classification Search
None
See application file for complete search history.

(56) References Cited

U.S. PATENT DOCUMENTS

| | | |
|---|---|---|
| 8,324,225 B2 | 12/2012 | Brain et al. |
| 8,415,355 B2 | 4/2013 | Brain et al. |
| 8,685,980 B2 | 4/2014 | Besong et al. |
| 8,962,630 B2 | 2/2015 | Brain et al. |
| 9,193,732 B2 | 11/2015 | Calienni et al. |
| 9,416,136 B2 | 8/2016 | Besong et al. |
| 9,868,739 B2 | 1/2018 | Calienni et al. |
| 10,336,763 B1 * | 7/2019 | Kamani ............... C07D 487/04 |
| 2014/0135312 A1 | 5/2014 | Besong et al. |
| 2015/0009976 A1 | 1/2015 | Kekki |
| 2018/0282342 A1 | 10/2018 | Chen et al. |
| 2021/0122754 A1 | 4/2021 | Thiriveedhi et al. |

FOREIGN PATENT DOCUMENTS

| | | | |
|---|---|---|---|
| CN | 105085533 A | 11/2015 | |
| EP | 3231805 A1 * | 10/2017 | ........... A61K 31/519 |
| EP | 3279201 A4 | 9/2018 | |
| WO | 01/47507 A2 | 7/2001 | |
| WO | 2003/053361 A2 | 7/2003 | |
| WO | 2005/023761 A2 | 3/2005 | |
| WO | 2006/008545 A2 | 1/2006 | |
| WO | 2007/014022 A1 | 2/2007 | |
| WO | 2007/075783 A2 | 7/2007 | |
| WO | 2010/020675 A1 | 2/2010 | |
| WO | 2011/133888 A1 | 10/2011 | |
| WO | 2012/064805 A1 | 5/2012 | |
| WO | 2012160034 A1 | 11/2012 | |
| WO | 2016091221 A1 | 6/2016 | |
| WO | WO2019040567 † | 8/2017 | |
| WO | 2019040567 A1 | 2/2019 | |
| WO | 2019/111160 A1 | 6/2019 | |
| WO | 2019/123364 A1 | 6/2019 | |
| WO | 2020152629 A1 | 7/2020 | |

OTHER PUBLICATIONS

Renoir et. al. (2013), Estrogen receptor signaling as a target for novel breast cancer therapeutics, Biochemical Pharmacology, 85, 449-465. (Year: 2013).*
International Search Report and Written Opinion for International Application No. PCT/IB2020/050544, mailed Jun. 25, 2020 (14 pages).
Ashizawa et al., "Science of Polymorphism Phenomena and Crystallization of Pharmaceutical Products", published by Maruzen Planet Co., Ltd., 2002, pp. 305-311 (English translation provided).
Berge et al., "Pharmaceutical Salts", J Pharm Sci. 66(1):1-19 (1977).
Serajuddin, "Salt formation to improve drug solubility," Adv Drug Deliv Rev. 59(7):603-16 (2007).
Stahl et al. eds., 2008, Handbook of pharmaceutical salts. Properties, selection and use (Wiley-VCH), pp. 265-327.
Bastin et al., "Salt Selection and Optimisation Procedures for Pharmaceutical New Chemical Entities," Organic Process Research & Development. 4(5):427-35 (2000).
Marcos Malumbres et al., "CDK inhibitors in cancer therapy: what is next?", Trends in Pharmacological Sciences, vol. 29, No. 1, pp. 16-21, 2008.
Cicenas et al., "Highlights of the Latest Advances in Research on CDK Inhibitors," Cancers. 6(4):2224-42 (2014).
Knockaert et al., "Pharmacological inhibitors of cyclin-dependent kinases," Trends Pharmacol Sci. 23(9):417-25 (2002).

(Continued)

*Primary Examiner* — Juliet C Switzer
*Assistant Examiner* — Dawanna Shar-Day White
(74) *Attorney, Agent, or Firm* — Derek Denhart

(57) ABSTRACT

Provided herein are new crystalline form(s) of succinate salt(s) of 7-Cyclopentyl-2-(5-piperazin-1-yl-pyridin-2-ylamino)-7H-pyrrolo[2,3-d]pyrimidine-6-carboxylic acid dimethylamide (also known as ribociclib), pharmaceutical compositions comprising the same, methods of treatment using the same and methods of making the same.

1 Claim, 16 Drawing Sheets

(56) References Cited

OTHER PUBLICATIONS

O'Leary et al., "Treating cancer with selective CDK4/6 inhibitors," Nat Rev Clin Oncol. 13(7):417-30 (2016).
Balbach et al., Pharmaceutical evaluation of early development candidates "the 100 mg-approach" International Journal of Pharmaceutics. 275(1-2):1-12 (2004).
Caira et al., "Crystalline Polymorphism of Organic Compounds," Weber E. et al. (eds) Design of Organic Solids, Topics in Current Chemistry. 198: (1998).
Singhal et al., "Drug polymorphism and dosage form design: a practical perspective," Advanced Drug Delivery Reviews. 56(3):335-47 (2004).
Bernstein, Polymorphism of Molecular Crystals, chapter 7.3.2, 324-330, 2007.
Berzins, et al., On the Formation of Droperidol Solvates: Characterization of Structure and Properties, Crystal Growth & Design, 14, 2654-2664, Apr. 16, 2014.
Burki, Ribociclib in HR-positive, HER2-negative breast cancer, The Lancet Oncology, 17, Nov. 2016.
Burris, Ribociclib for the treatment of hormone receptorpositive, human epidermal growth factor receptor 2-negative advanced breast cancer, Expert Review of Anticancer Therapy, 18(3), 201-213, Feb. 19, 2018.
Kummerer, Pharmaceuticals in the environment, Annual Review of Environment and Resources, 35, 57-75, Aug. 18, 2010.
Kuznetsova, High-resolution X-Ray Analysis, Irkutsk State University, 2005.
Lopez-Tarruella, et al., Ribociclib for the treatment of advanced hormone receptor-positive, HER2-negative breast cancer, Future Oncology, 13-24, 2137-2149, Oct. 2017.
Mashkovsky, Medicaments: A Guide for Doctors, Lekarstvennye Sredstva, 15th edition, 10-11, 2005.
Morissette, et al., High-throughput crystallization: Polymorphs, salts, co-crystals and solvates of pharmaceutical solids, Advanced Drug Delivery Reviews, 56, 275-300, 2004.
Reichardt, Solvents and Solvent Effects in Organic Chemistry, section A5, 611-614, 1988.
Tian, et al., Factors affecting crystallization of hydrates, Journal of Pharmacy and Pharmacology, 62, 1534-1546, 2010.
U.S. Appl. No. 62/555,170.
Variankaval, et al., From form to function: Crystallization of active pharmaceutical ingredients, AlChE Journal, 54 (7), 1682-1688, Jul. 2008.
Ashizawa, Optimisation of salts/crystal forms and crystallization technology, Pharm Tech Japan, 2002, 18(10), 81-96.
Hirayama, General methods of crystallization, Handbook on Organic Compound Crystals Process, 2008. chapter 3, 36-43.
Nagase, Preparation of water-soluble organic compounds by salt formation, Latest Drug Discovery Chemistry, 1999, chapter 34, 347-354.
Aaltonen, et al., Solid form screening—A review, European Journal of Pharmaceutics and Biopharmaceutics, 71 (1), 23-37, 2009.
Esteva, Ribociclib Plus Fulvestrant for HR+, HE, Advanced Breast Cancer, 36-37, 2018.
Sarma, et al., Solid forms of pharmaceuticals: Polymorphs, salts and cocrystals, Korean J. Chem. Eng., 28(2), 315-322, Feb. 2011.
Zhukova, et al., Ribociclib in the 1st line of therapy for hormone-sensitive breast cancer, Clinical Oncology, 20(2), 38-41, 2018.
Bavin, Polymorphism in Process Development, Chemistry and Industry, 527-529, Aug. 21, 1989.
Byrn, et al., Pharmaceutical Solids: A Strategic Approach to Regulatory Considerations, Pharmaceutical Research, 12(7), 945-954, 1995.
Carlson, et al., An integrated high throughput workflow for pre-formulations: Polymorph and salt selection studies, Pharm. Chem, Drug Development, 10-15, 2003.
Takada, API form screening and selection in drug discovery stage, Pharm Stage, 6(10), 20-25, 2007.
Kawaguchi, et al., Drug and crystal polymorphism, Journal of Human Environmental Engineering, 4(2), 310-317, 2002.
Yamano, Approach to Crystal Polymorph in Process Research of New Drug, Journal of Synthetic Organic Chemistry, 65, 907-913, 2007.
Ashizawa, Chemistry of polymorphism and crystallization of pharmaceuticals, 273,278,305-317, 2002.
Vergani et al., "Solid State Forms of Ribociclib Succinate," U.S. Appl. No. 62/555,170, filed Sep. 7, 2017, 24 pages, published Feb. 28, 2019, WIPO Patentscope URL I8LqIYWXduSdBWwWvBGT JHdERrcKYazVyMHwWFP66Dhla9JeMfx8q6RnyQH69ufr-DEPooB_vjeHasiZTyJh5VLO_V-wmDaO32-lj74ni1ZNjLbVSEVqb4PcCSlyo0Yi (wipo.int).†

\* cited by examiner
† cited by third party

CRYSTALLINE FORMS OF A SUCCINATE SALT OF 7-CYCLOPENTYL-2-(5-PIPERAZIN-1-YL-PYRIDIN-2-YLAMINO)-7H-PYRROLO[2,3-D]PYRIMIDINE-6-CARBOXYLIC ACID DIMETHYLAMIDE

RELATED APPLICATIONS

This application is a U.S. national stage of International Application No. PCT/IB2020/050544, filed Jan. 23, 2020, which claims priority to, and the benefit of, U.S. Application Ser. No. 62/795,799, filed Jan. 23, 2019, the content of which is hereby incorporated by reference in its entirety.

FIELD OF THE INVENTION

This invention relates to new crystalline forms of succinate salt(s) of 7-Cyclopentyl-2-(5-piperazin-1-yl-pyridin-2-ylamino)-7H-pyrrolo[2,3-d]pyrimidine-6-carboxylic acid dimethylamide, pharmaceutical compositions comprising the same, methods of treatment using the same and methods for obtaining such forms.

BACKGROUND

The compound 7-Cyclopentyl-2-(5-piperazin-1-yl-pyridin-2-ylamino)-7H-pyrrolo[2,3-d]pyrimidine-6-carboxylic acid dimethylamide of Formula (I)

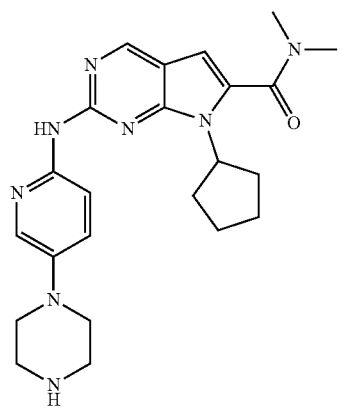

(I)

and its synthesis is specifically described in WO 2010/020675 A1, Example 74. WO2010/020675 discloses that compound of Formula (I) has valuable pharmacological properties and can be used, for example, (1) as inhibitors of cyclin dependent kinases, (in particular, cyclin dependent kinases selected from CDK1, CDK2, CDK3, CDK4, CDK5, CDK6 and CDK9); and (2) as modulators and/or inhibitors of glycogen synthase kinase-3 (GSK-3). The compound of Formula (I) is also known as ribociclib.

WO2012/064805 (PCT patent application PCT/US2011/059890) discloses succinate salt of 7-Cyclopentyl-2-(5-piperazin-1-yl-pyridin-2-ylamino)-7H-pyrrolo[2,3-d]pyrimidine-6-carboxylic acid dimethylamide described by Formula (II):

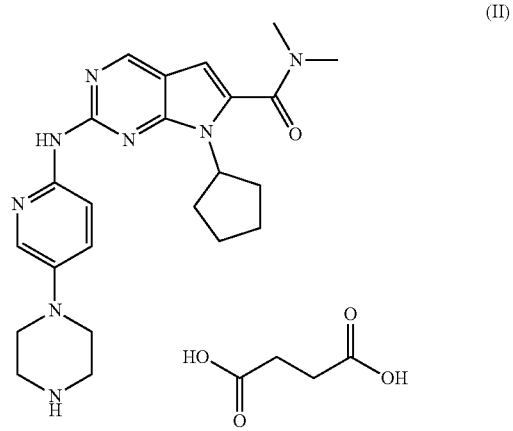 [SMILES: CN(C)C(=O)c1cc2cnc(Nc3ccc(N4CCNCC4)cn3)nc2n1C1CCCC1 ; O=C(O)CCC(=O)O]

(II)

SUMMARY OF THE INVENTION

In one aspect, the present invention is directed to new crystalline forms of 7-Cyclopentyl-2-(5-piperazin-1-yl-pyridin-2-ylamino)-7H-pyrrolo[2,3-d]pyrimidine-6-carboxylic acid dimethylamide succinate, i.e., new crystalline form(s) of ribociclib succinate.

In one embodiment, the new crystalline form is Modification E, also referred to as Mod. E, or Form E. Modification E is an anhydrous crystalline form of ribociclib succinate.

In another embodiment, the new crystalline form is Modification F, also referred to as Mod. F, or Form F. Modification F is an anhydrous ribociclib hemisuccinate.

In yet another embodiment, the new crystalline form is called Modification $H_B$, or Mod. $H_B$, or Form $H_B$. Modification $H_B$ is a ribociclib succinate dihydrate.

In a further embodiment, the new crystalline form is called Modification $H_A$, or Mod. $H_A$, or Form $H_A$. Modification $H_A$ is a hydrated form of ribociclib hemisuccinate (e.g., hemihydrate, or monohydrate, or a hydrate with a ratio of ribociclib:water ranging between 2:1 and 1:1 or between 3:1 and 2:1, or between 3:2 and 2:1).

As used herein, the term "hemisuccinate" refers to a salt having a stoichiometric ratio of two molecules of compound of Formula (I) to one molecule of succinate counterion or succinic acid. The hemisuccinate of compound of Formula (I) may be represented as shown below.

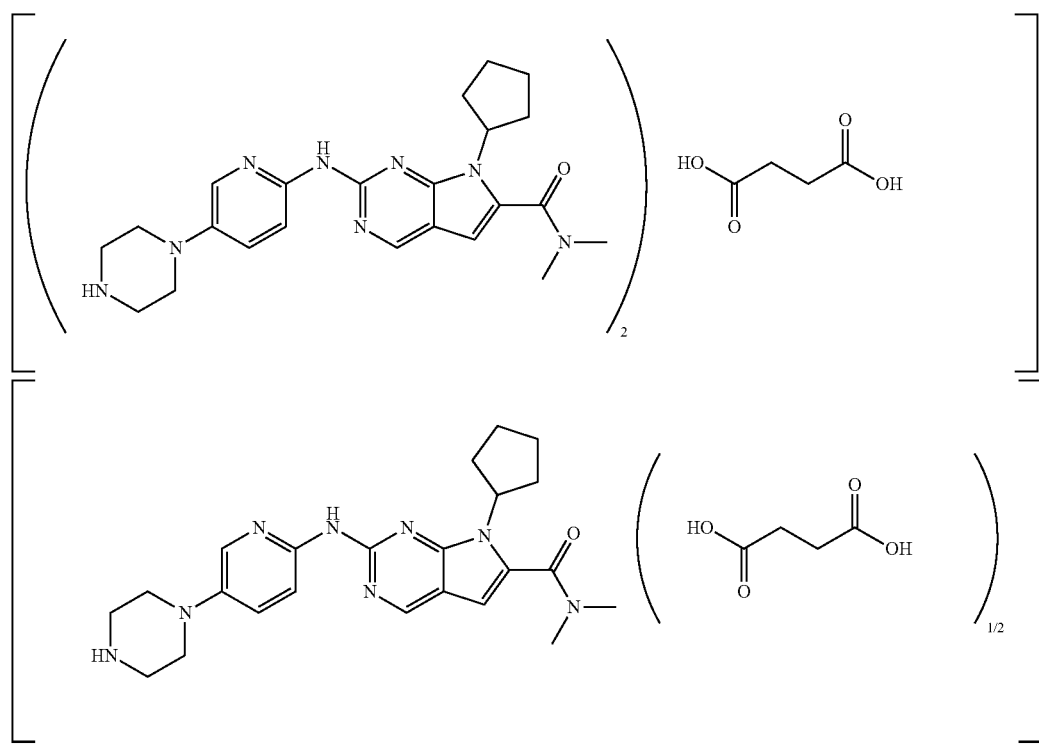

As used herein and unless otherwise specified, the term "succinate" or "succinate salt" refers to a salt having a viable stoichiometric ratio (e.g., 1:1, 1:2, 2:1, etc.) of the compound of Formula (I) (i.e., ribociclib) to succinate counterion or succinic acid. In other words, the term "succinate" or "succinate salt" includes, but is not limited to, hemisuccinate and the succinate described by Formula (II) herein (or a monosuccinate). Similarly, the term "hydrate" or "hydrated form", unless otherwise specified, refers to a hydrate having a viable stoichiometric ratio (e.g., 1:1, 1:2, 2:1, etc.) of the compound of Formula (I) (i.e., ribociclib) to water molecule, which includes but is not limited to hemihydrate, monohydrate, or dihydrate.

The names used herein to characterize a specific form, e.g. "E, F, $H_A$, or $H_B$" etc., should not be considered limiting with respect to any other substance possessing similar or identical physical and chemical characteristics, but rather it should be understood that these designations are mere identifiers that should be interpreted according to the characterization information also presented herein.

In another aspect, the present invention is also directed to pharmaceutical compositions comprising the new crystalline form(s) (Modification E, Modification F, Modification $H_B$, or Modification $H_A$) of ribociclib succinate.

In one embodiment, the present invention is directed to a pharmaceutical composition comprising ribociclib, or salt thereof, wherein Modification E is about 3% w/w or more of the total amount of ribociclib, or salt thereof.

In one embodiment, the present invention is directed to a pharmaceutical composition comprising ribociclib, or salt thereof, wherein Modification E is about 5% w/w or more of the total amount of ribociclib, or salt thereof.

In one embodiment, the present invention is directed to a pharmaceutical composition comprising ribociclib, or salt thereof, wherein Modification E is about 10% w/w or more of the total amount of ribociclib, or salt thereof.

In one embodiment, the present invention is directed to a pharmaceutical composition comprising ribociclib, or salt thereof, wherein Modification E is about 20% w/w or more of the total amount of ribociclib, or salt thereof.

In one embodiment, the present invention is directed to a pharmaceutical composition comprising ribociclib, or salt thereof, wherein Modification E is about 30% w/w or more of the total amount of ribociclib, or salt thereof.

In one embodiment, the present invention is directed to a pharmaceutical composition comprising ribociclib, or salt thereof, wherein Modification E is about 40% w/w or more of the total amount of ribociclib, or salt thereof.

In one embodiment, the present invention is directed to a pharmaceutical composition comprising ribociclib, or salt thereof, wherein Modification E is about 50% w/w or more of the total amount of ribociclib, or salt thereof.

In one embodiment, the present invention is directed to a pharmaceutical composition comprising ribociclib, or salt thereof, wherein Modification E is about 60% w/w or more of the total amount of ribociclib, or salt thereof.

In one embodiment, the present invention is directed to a pharmaceutical composition comprising ribociclib, or salt thereof, wherein Modification E is about 70% w/w or more of the total amount of ribociclib, or salt thereof.

In one embodiment, the present invention is directed to a pharmaceutical composition comprising ribociclib, or salt thereof, wherein Modification E is about 80% w/w or more of the total amount of ribociclib, or salt thereof.

In one embodiment, the present invention is directed to a pharmaceutical composition comprising ribociclib, or salt thereof, wherein Modification E is about 90% w/w or more of the total amount of ribociclib, or salt thereof.

In one embodiment, the present invention is directed to a pharmaceutical composition comprising ribociclib, or salt thereof, wherein the ribociclib, or salt thereof is substantially pure Modification E.

In one embodiment, the present invention is directed to a pharmaceutical composition comprising ribociclib, or salt thereof, wherein Modification E is about 3% to about 90% w/w of the total amount of ribociclib, or salt thereof.

In one embodiment, the present invention is directed to a pharmaceutical composition comprising ribociclib, or salt thereof, wherein Modification E is about 3% to about 80% w/w of the total amount of ribociclib, or salt thereof.

In one embodiment, the present invention is directed to a pharmaceutical composition comprising ribociclib or salt thereof wherein Modification E is about 3% to about 70% w/w of the total amount of ribociclib or salt thereof.

In one embodiment, the present invention is directed to a pharmaceutical composition comprising ribociclib or salt thereof wherein Modification E is about 3% to about 60% w/w of the total amount of ribociclib or salt thereof.

In one embodiment, the present invention is directed to a pharmaceutical composition comprising ribociclib or salt thereof wherein Modification E is about 3% to about 50% w/w of the total amount of ribociclib or salt thereof.

In one embodiment, the present invention is directed to a pharmaceutical composition comprising ribociclib or salt thereof wherein Modification E is about 3% to about 40% w/w of the total amount of ribociclib or salt thereof.

In one embodiment, the present invention is directed to a pharmaceutical composition comprising ribociclib or salt thereof wherein Modification E is about 3% to about 30% w/w of the total amount of ribociclib or salt thereof.

In one embodiment, the present invention is directed to a pharmaceutical composition comprising ribociclib or salt thereof wherein Modification E is about 20% to about 30% w/w of the total amount of ribociclib or salt thereof.

In one embodiment, the present invention is directed to a pharmaceutical composition comprising ribociclib or salt thereof wherein Modification E is about 30% to about 40% w/w of the total amount of ribociclib or salt thereof.

In one embodiment, the present invention is directed to a pharmaceutical composition comprising ribociclib or salt thereof wherein Modification E is about 3% to about 20% w/w of the total amount of ribociclib or salt thereof.

In one embodiment, the present invention is directed to a pharmaceutical composition comprising ribociclib, or salt thereof, wherein Modification E is up to 10% (e.g., less than about 10%, about 0% to about 10%, about 0.5%-10%, or up to about 5%, up to about 3% or about 3-5%) w/w of the total amount of ribociclib, or salt thereof.

The present invention is also directed to methods of treatment using the new anhydrous crystalline form Modification E of ribociclib succinate.

In one embodiment, the present invention is directed to a pharmaceutical composition comprising ribociclib, or salt thereof, wherein Modification F is about 3% w/w or more of the total amount of ribociclib, or salt thereof.

In one embodiment, the present invention is directed to a pharmaceutical composition comprising ribociclib, or salt thereof, wherein Modification F is about 5% w/w or more of the total amount of ribociclib, or salt thereof.

In one embodiment, the present invention is directed to a pharmaceutical composition comprising ribociclib, or salt thereof, wherein Modification F is about 10% w/w or more of the total amount of ribociclib, or salt thereof.

In one embodiment, the present invention is directed to a pharmaceutical composition comprising ribociclib, or salt thereof, wherein Modification F is about 20% w/w or more of the total amount of ribociclib, or salt thereof.

In one embodiment, the present invention is directed to a pharmaceutical composition comprising ribociclib, or salt thereof, wherein Modification F is about 30% w/w or more of the total amount of ribociclib, or salt thereof.

In one embodiment, the present invention is directed to a pharmaceutical composition comprising ribociclib, or salt thereof, wherein Modification F is about 40% w/w or more of the total amount of ribociclib, or salt thereof.

In one embodiment, the present invention is directed to a pharmaceutical composition comprising ribociclib, or salt thereof, wherein Modification F is about 50% w/w or more of the total amount of ribociclib, or salt thereof.

In one embodiment, the present invention is directed to a pharmaceutical composition comprising ribociclib, or salt thereof, wherein Modification F is about 60% w/w or more of the total amount of ribociclib, or salt thereof.

In one embodiment, the present invention is directed to a pharmaceutical composition comprising ribociclib, or salt thereof, wherein Modification F is about 70% w/w or more of the total amount of ribociclib, or salt thereof.

In one embodiment, the present invention is directed to a pharmaceutical composition comprising ribociclib, or salt thereof, wherein Modification F is about 80% w/w or more of the total amount of ribociclib, or salt thereof.

In one embodiment, the present invention is directed to a pharmaceutical composition comprising ribociclib, or salt thereof, wherein Modification F is about 90% w/w or more of the total amount of ribociclib, or salt thereof.

In one embodiment, the present invention is directed to a pharmaceutical composition comprising ribociclib, or salt thereof, wherein the ribociclib, or salt thereof is substantially pure Modification F.

In one embodiment, the present invention is directed to a pharmaceutical composition comprising ribociclib, or salt thereof, wherein Modification F is about 3% to about 90% w/w of the total amount of ribociclib, or salt thereof.

In one embodiment, the present invention is directed to a pharmaceutical composition comprising ribociclib, or salt thereof, wherein Modification F is about 3% to about 80% w/w of the total amount of ribociclib, or salt thereof.

In one embodiment, the present invention is directed to a pharmaceutical composition comprising ribociclib or salt thereof wherein Modification F is about 3% to about 70% w/w of the total amount of ribociclib or salt thereof.

In one embodiment, the present invention is directed to a pharmaceutical composition comprising ribociclib or salt thereof wherein Modification F is about 3% to about 60% w/w of the total amount of ribociclib or salt thereof.

In one embodiment, the present invention is directed to a pharmaceutical composition comprising ribociclib or salt thereof wherein Modification F is about 3% to about 50% w/w of the total amount of ribociclib or salt thereof.

In one embodiment, the present invention is directed to a pharmaceutical composition comprising ribociclib or salt thereof wherein Modification F is about 3% to about 40% w/w of the total amount of ribociclib or salt thereof.

In one embodiment, the present invention is directed to a pharmaceutical composition comprising ribociclib or salt thereof wherein Modification F is about 3% to about 30% w/w of the total amount of ribociclib or salt thereof.

In one embodiment, the present invention is directed to a pharmaceutical composition comprising ribociclib or salt thereof wherein Modification F is about 20% to about 30% w/w of the total amount of ribociclib or salt thereof.

In one embodiment, the present invention is directed to a pharmaceutical composition comprising ribociclib or salt thereof wherein Modification F is about 30% to about 40% w/w of the total amount of ribociclib or salt thereof.

In one embodiment, the present invention is directed to a pharmaceutical composition comprising ribociclib or salt thereof wherein Modification F is about 3% to about 20% w/w of the total amount of ribociclib or salt thereof.

In one embodiment, the present invention is directed to a pharmaceutical composition comprising ribociclib, or salt thereof, wherein Modification F is up to 10% (e.g., less than about 10%, about 0% to about 10%, about 0.5%-10%, or up to about 5%, up to about 3% or about 3-5%) w/w of the total amount of ribociclib, or salt thereof.

In embodiments, the present invention is also directed to methods of treatment using the new anhydrous crystalline form Modification F of ribociclib hemisuccinate.

In one embodiment, the present invention is directed to a pharmaceutical composition comprising ribociclib or salt thereof wherein Modification $H_B$ is about 3% w/w or more of the total amount of ribociclib or salt thereof.

In one embodiment, the present invention is directed to a pharmaceutical composition comprising ribociclib or salt thereof wherein Modification $H_B$ is about 5% w/w or more of the total amount of ribociclib or salt thereof.

In one embodiment, the present invention is directed to a pharmaceutical composition comprising ribociclib or salt thereof wherein Modification $H_B$ is about 10% w/w or more of the total amount of ribociclib or salt thereof.

In one embodiment, the present invention is directed to a pharmaceutical composition comprising ribociclib or salt thereof wherein Modification $H_B$ is about 20% w/w or more of the total amount of ribociclib or salt thereof.

In one embodiment, the present invention is directed to a pharmaceutical composition comprising ribociclib or salt thereof wherein Modification $H_B$ is about 30% w/w or more of the total amount of ribociclib or salt thereof.

In one embodiment, the present invention is directed to a pharmaceutical composition comprising ribociclib or salt thereof wherein Modification $H_B$ is about 40% w/w or more of the total amount of ribociclib or salt thereof.

In one embodiment, the present invention is directed to a pharmaceutical composition comprising ribociclib or salt thereof wherein Modification $H_B$ is about 50% w/w or more of the total amount of ribociclib or salt thereof.

In one embodiment, the present invention is directed to a pharmaceutical composition comprising ribociclib or salt thereof wherein Modification $H_B$ is about 60% w/w or more of the total amount of ribociclib or salt thereof.

In one embodiment, the present invention is directed to a pharmaceutical composition comprising ribociclib or salt thereof wherein Modification $H_B$ is about 70% w/w or more of the total amount of ribociclib or salt thereof.

In one embodiment, the present invention is directed to a pharmaceutical composition comprising ribociclib or salt thereof wherein Modification $H_B$ is about 80% w/w or more of the total amount of ribociclib or salt thereof.

In one embodiment, the present invention is directed to a pharmaceutical composition comprising ribociclib or salt thereof wherein Modification $H_B$ is about 90% w/w or more of the total amount of ribociclib or salt thereof.

In one embodiment, the present invention is directed to a pharmaceutical composition comprising ribociclib or salt thereof wherein the ribociclib or salt thereof is substantially pure Modification $H_B$.

In one embodiment, the present invention is directed to a pharmaceutical composition comprising ribociclib or salt thereof wherein Modification $H_B$ is about 10% to about 90% w/w of the total amount of ribociclib or salt thereof.

In one embodiment, the present invention is directed to a pharmaceutical composition comprising ribociclib or salt thereof wherein Modification $H_B$ is about 10% to about 80% w/w of the total amount of ribociclib or salt thereof.

In one embodiment, the present invention is directed to a pharmaceutical composition comprising ribociclib or salt thereof wherein Modification $H_B$ is about 10% to about 70% w/w of the total amount of ribociclib or salt thereof.

In one embodiment, the present invention is directed to a pharmaceutical composition comprising ribociclib or salt thereof wherein Modification $H_B$ is about 10% to about 60% w/w of the total amount of ribociclib or salt thereof.

In one embodiment, the present invention is directed to a pharmaceutical composition comprising ribociclib or salt thereof wherein Modification $H_B$ is about 10% to about 50% w/w of the total amount of ribociclib or salt thereof.

In one embodiment, the present invention is directed to a pharmaceutical composition comprising ribociclib or salt thereof wherein Modification $H_B$ is about 10% to about 40% w/w of the total amount of ribociclib or salt thereof.

In one embodiment, the present invention is directed to a pharmaceutical composition comprising ribociclib or salt thereof wherein Modification $H_B$ is about 10% to about 30% w/w of the total amount of ribociclib or salt thereof.

In one embodiment, the present invention is directed to a pharmaceutical composition comprising ribociclib or salt thereof wherein Modification $H_B$ is about 20% to about 30% w/w of the total amount of ribociclib or salt thereof.

In one embodiment, the present invention is directed to a pharmaceutical composition comprising ribociclib or salt thereof wherein Modification $H_B$ is about 30% to about 40% w/w of the total amount of ribociclib or salt thereof.

In one embodiment, the present invention is directed to a pharmaceutical composition comprising ribociclib or salt thereof wherein Modification $H_B$ is about 10% to about 20% w/w of the total amount of ribociclib or salt thereof.

The concentration (e.g., weight percentage or molar percentage) of each specific form disclosed herein (i.e., Modification E, F, $H_A$, or $H_B$) in a pharmaceutical composition can be measured and determined by conventional methods such as XRPD (X-ray powder diffraction) data analysis.

The present invention is also directed to methods of treatment using the new crystalline form Modification $H_B$ of ribociclib succinate.

The present invention is also directed to a pharmaceutical composition comprising a combination of Modification A and Modification of E of ribociclib succinate.

The present invention is also directed to a pharmaceutical composition comprising a combination of Modification A and Modification of $H_B$ of ribociclib succinate.

The present invention is also directed to a pharmaceutical composition comprising a combination of Modification E and Modification of $H_A$ of ribociclib succinate.

DETAILED DESCRIPTION OF THE INVENTION

Figure 1:
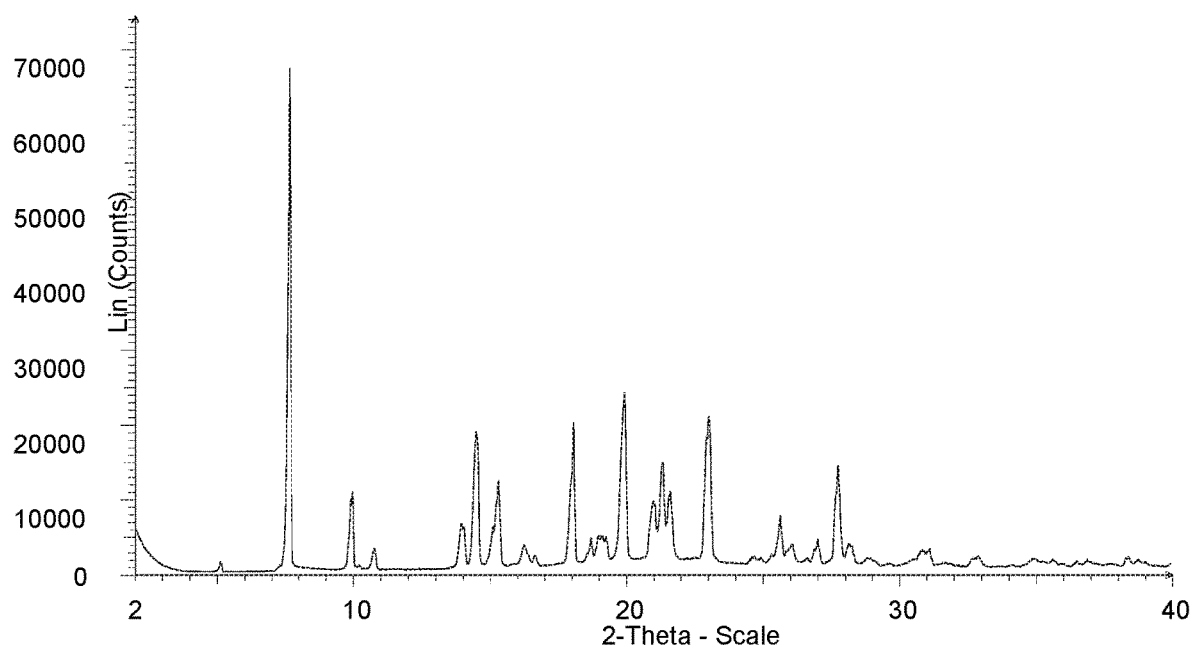
FIG. 1 shows the XRPD diffractogram of Modification A of ribociclib succinate recorded in reflection mode.

The present invention is directed to several new crystalline form(s) of succinate salt(s) of 7-cyclopentyl-2-(5-piperazin-1-yl-pyridin-2-ylamino)-7H-pyrrolo[2,3-d]pyrimidine-6-carboxylic acid dimethylamide. 7-cyclopentyl-2-(5-piperazin-1-yl-pyridin-2-ylamino)-7H-pyrrolo[2,3-d]pyrimidine-6-carboxylic acid dimethylamide is also known by its INN ribociclib.

In one embodiment, the new crystalline form is Modification E, also referred to as Mod. E, or Form E. Modification E is an anhydrous ribociclib succinate and is described by Formula (II):

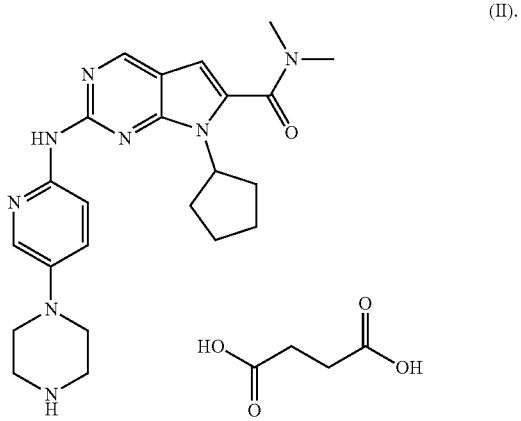 [SMILES: CN(C)C(=O)c1cc2cnc(Nc3ccc(N4CCNCC4)cn3)nc2n1C1CCCC1 ; O=C(O)CCC(=O)O]

(II).

In another embodiment, the new crystalline form is Modification F, also referred to as Mod. F, or Form F. Modification F is an anhydrous ribociclib hemisuccinate.

In yet another embodiment, the new crystalline form is called Modification $H_B$, or Mod. $H_B$, or Form $H_B$. Modification $H_B$ is a ribociclib succinate dihydrate.

In a further embodiment, the new crystalline form is called Modification $H_A$, or Mod. $H_A$, or Form $H_A$. Modification $H_A$ is a hydrated form of ribociclib hemisuccinate.

The present invention is further directed to pharmaceutical compositions comprising Modification E and at least one pharmaceutically acceptable carrier, diluent, vehicle or excipient.

The present invention is further directed to pharmaceutical compositions comprising Modification $H_B$ and at least one pharmaceutically acceptable carrier, diluent, vehicle or excipient.

The present invention is further directed to pharmaceutical compositions comprising Modification $H_A$ and at least one pharmaceutically acceptable carrier, diluent, vehicle or excipient.

The present invention is also directed to a method of treating a disease which responds to an inhibition of cyclin dependent kinases, (in particular, cyclin dependent kinases selected from CDK1, CDK2, CDK3, CDK4, CDK5, CDK6 and CDK9) comprising the step of administering to a subject in need of such treatment a therapeutically effective amount of Modification E.

The present invention is also directed to a method of treating a disease which responds to an inhibition of cyclin dependent kinases, (in particular, cyclin dependent kinases selected from CDK1, CDK2, CDK3, CDK4, CDK5, CDK6 and CDK9) comprising the step of administering to a subject in need of such treatment a therapeutically effective amount of Modification $H_B$.

The present invention is also directed to a method of treating a disease which responds to an inhibition of cyclin dependent kinases, (in particular, cyclin dependent kinases selected from CDK1, CDK2, CDK3, CDK4, CDK5, CDK6 and CDK9) comprising the step of administering to a subject in need of such treatment a therapeutically effective amount of Modification $H_A$.

Such disease which responds to an inhibition of cyclin dependent kinases includes, but is not limited to breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; leukemias, hyperplasias, stomach cancer, colon cancer, larynx cancer, lymphatic system cancer, genitourinary tract cancer, bone cancer, prostate cancer, small-cell lung cancer, glioma cancer, colorectal cancer, kidney cancer, epidermis cancer, liver cancer, esophagus cancer, hematopoietic cancer, lymphoma, myeloma, thyroid follicular cancer; a tumor of mesenchymal origin, for example fibrosarcoma or rhabdomyosarcoma; a tumor of the central or peripheral nervous system, for example astrocytoma, neuroblastoma, glioma or schwannoma; melanoma; seminoma; teratocarcinoma; osteosarcoma; xeroderma pigmentosum; keratoacanthoma; thyroid follicular cancer; Kaposi's sarcoma, chronic lymphocytic leukaemia, mantle cell lymphoma, large B cell lymphoma.

In one particular embodiment, the disease is hormone receptor (HR)-positive, human epidermal growth factor receptor 2 (HER2)-negative advanced or metastatic breast cancer postmenopausal women.

As used herein, "substantially pure," when used in reference to a form, means a compound having a purity greater than 90 weight %, including greater than 90, 91, 92, 93, 94, 95, 96, 97, 98, and 99 weight %, and also including equal to about 100 weight % of a compound, based on the weight of the compound. The remaining material comprises other form(s) of the compound, and/or reaction impurities and/or processing impurities arising from its preparation. For example, a crystalline form of ribociclib succinate may be deemed substantially pure in that it has a purity greater than 90 weight %, as measured by means that are at this time known and generally accepted in the art (e.g., European Pharmacopoeia or USP), where the remaining less than 10 weight % of material comprises other form(s) of ribociclib succinate and/or reaction impurities and/or processing impurities.

A "therapeutically effective amount" is intended to mean the amount of the compound that, when administered to a subject in need thereof, is sufficient to effect treatment for disease conditions alleviated by the inhibition of cyclin dependent kinases activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The "at least one pharmaceutically acceptable carrier, diluent, vehicle or excipient" can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols.

The term "substantially the same" or "substantially in accordance with", with reference to X-ray diffraction peak positions, means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The use of the articles "a", "an", and "the" in both the description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of".

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 10% more or less than the specified value. In another embodiment, the term "about" refers to a range of values which are 5% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the terms "between X and Y" and "range from X to Y, are inclusive of X and Y and the integers there between. On the other hand, when a series of individual values are referred to in the disclosure, any range including any of the two individual values as the two end points is also conceived in this disclosure (except for the 2-Theta values in the XRPD patterns). For example, the expression "a purity of 90, 91, 92, 93, 94, 95, 96, 97, 98, and 99 weight %," can also mean "a purity ranging from 90 wt % to 95 wt %", "a purity ranging from 93 wt % to 97 wt %", or "a purity ranging from 90 wt % to 99 wt %".

Modification E is anhydrous. The crystalline form disclosed in the WO2012/064805 is referred to as Modification A or Mod. A hereafter.

Modification E, Modification F, Modification $H_A$, Modification $H_B$ and/or the comparator Modification A are characterized by various methods, including single X-ray data, X-ray powder diffraction (XRPD), DSC, Karl Fischer titration etc.

In one embodiment, the Modification E exhibits an X-ray powder diffraction pattern having characteristic peaks expressed in degrees 2-Theta at angles of 11.0°+/−0.2°, 13.0°+/−0.2°, and 17.2°+/−0.2°. In another embodiment, Modification E exhibits an X-ray powder diffraction pattern having at least four characteristic peaks expressed in degrees 2-Theta selected from 11.0°+/−0.2°, 13.0°+/−0.2°, 17.2°+/−0.2°, 20.0°+/−0.2°, and 23.0°+/−0.2°. In yet another embodiment, Modification E exhibits an X-ray powder diffraction pattern having at least five characteristic peaks expressed in degrees 2-Theta selected from 8.8°+/−0.2°, 11.0°+/−0.2°, 13.0°+/−0.2°, 13.7°+/−0.2°, 15.7°+/−0.2°, 17.2°+/−0.2°, 18.7°+/−0.2°, 20.0°+/−0.2°, 21.1°+/−0.2°, 23.0°+/−0.2°, and 24.9°+/−0.2°. In still another embodiment, Modification E exhibits an X-ray powder diffraction pattern having at least seven characteristic peaks expressed in degrees 2-Theta selected from 7.9°+/−0.2°, 8.8°+/−0.2°, 11.0°+/−0.2°, 12.4°+/−0.2°, 13.0°+/−0.2°, 13.7°+/−0.2°, 15.7°+/−0.2°, 17.2°+/−0.2°, 18.7°+/−0.2°, 20.0°+/−0.2°, 21.1°+/−0.2°, 23.0°+/−0.2°, and 24.9°+/−0.2°. In a further embodiment, Modification E exhibits an X-ray powder diffraction pattern substantially in accordance with FIG. 2 or Table 4.

In one embodiment, the Modification F exhibits an X-ray powder diffraction pattern having characteristic peaks expressed in degrees 2-Theta at angles of 4.9°+/−0.2°, 11.9°+/−0.2°, and 12.6°+/−0.2° (CuKα λ=1.5406 Å). In another embodiment, Modification F exhibits an X-ray powder diffraction pattern having at least three characteristic peaks expressed in degrees 2-Theta selected from 4.9°+/−0.2°, 11.9°+/−0.2°, 12.6°+/−0.2° and 22.8°+/−0.2°. In yet another embodiment, Modification F exhibits an X-ray powder diffraction pattern having at least four characteristic peaks expressed in degrees 2-Theta selected from 4.9°+/−0.2°, 11.9°+/−0.2°, 12.6°+/−0.2°, 22.8°+/−0.2° and 26.6°+/−0.2°. In still another embodiment, Modification F exhibits an X-ray powder diffraction pattern having at least five characteristic peaks expressed in degrees 2-Theta selected from 4.9°+/−0.2°, 11.9°+/−0.2°, 12.6°+/−0.2°, 22.8°+/−0.2°, 26.6°+/−0.2° and 29.4°+/−0.2°. In a further embodiment, Modification F exhibits an X-ray powder diffraction pattern substantially in accordance with FIG. 3 or Table 5.

In one embodiment, the Modification $H_B$ exhibits an X-ray powder diffraction pattern having characteristic peaks expressed in degrees 2-Theta at angles of 6.4°+/−0.2° and 20.6°+/−0.2°. In another embodiment, Modification $H_B$ exhibits an X-ray powder diffraction pattern having at least three characteristic peaks expressed in degrees 2-Theta selected from 6.4°+/−0.2°, 20.1°+/−0.2°, 20.6°+/−0.2°, 22.7°+/−0.2°, and 26.5°+/−0.2°. In yet another embodiment, Modification $H_B$ exhibits an X-ray powder diffraction pattern having at least five characteristic peaks expressed in degrees 2-Theta selected from 6.4°+/−0.2°, 7.4°+/−0.2°, 10.1°+/−0.2°, 10.7°+/−0.2°, 11.9°+/−0.2°, 20.1°+/−0.2°, 20.6°+/−0.2°, 22.7°+/−0.2°, 26.5°+/−0.2°, and 33.9°+/−0.2°. In a further embodiment, Modification $H_B$ exhibits an X-ray powder diffraction pattern substantially in accordance with FIG. 4 or Table 6.

Figure 5:
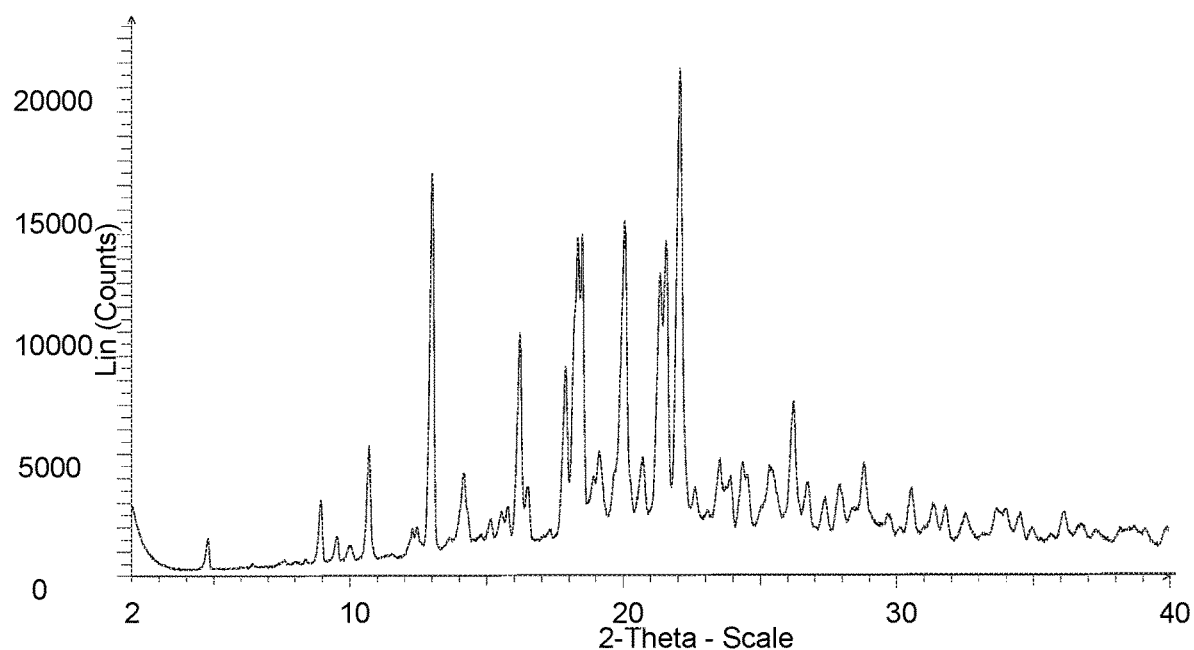
FIG. 5 shows the XRPD diffractogram of the Modification $H_A$ of ribociclib succinate recorded in reflection mode.

In one embodiment, the Modification $H_A$ exhibits an X-ray powder diffraction pattern having characteristic peaks expressed in degrees 2-Theta at angles of 4.7°+/−0.2°, 18.5°+/−0.2°, and 22.1°+/−0.2 In another embodiment, Modification $H_A$ exhibits an X-ray powder diffraction pattern having at least four characteristic peaks expressed in degrees 2-Theta selected from 4.7°+/−0.2°, 13.0°+/−0.2°, 18.5°+/−0.2°, 20.0°+/−0.2°, 21.6°+/−0.2°, and 22.1°+/−0.2°. In yet another embodiment, Modification $H_A$ exhibits an X-ray powder diffraction pattern having at least six characteristic peaks expressed in degrees 2-Theta selected from 4.7°+/−0.2°, 10.7°+/−0.2°, 13.0°+/−0.2°, 16.2°+/−0.2°, 17.9°+/−0.2°, 18.5°+/−0.2°, 20.0°+/−0.2°, 21.6°+/−0.2°, 22.1°+/−0.2°, 26.2°+/−0.2° and 28.8°+/−0.2°. In still another embodiment, Modification $H_A$ exhibits an X-ray powder diffraction pattern having at least eight characteristic peaks expressed in degrees 2-Theta selected from 4.7°+/−0.2°, 8.9°+/−0.2°, 10.7°+/−0.2°, 13.0°+/−0.2°, 16.2°+/−0.2°, 17.9°+/−0.2°, 18.5°+/−0.2°, 20.0°+/−0.2°, 21.6°+/−0.2°, 22.1°+/−0.2°, 26.2°+/−0.2° and 28.8°+/−0.2°. In a further embodiment, Modification $H_A$ exhibits an X-ray powder diffraction pattern substantially in accordance with FIG. 5 or Table 7.

In another aspect, the invention relates to a process of making Modification E comprising: providing a solution of about 0.1 mg/mL to about 1.0 mg/mL (e.g., about 0.2-0.8 mg/mL, 03-0.7 mg/mL, 0.35-0.5 mg/mL, 0.4-0.6 mg/mL) ribociclib monosuccinate in an organic solvent (e.g., an alcohol such as isopropanol) wherein the solution is substantively free of water and maintained (e.g., under shaking) at a first temperature ranging between about 50° C. and about 80° C. (e.g., about 55-65° C., about 60° C.) for a first period of time (e.g., at least about 3 days, 5 days, 7 days, 10 days, 14 days, or at least about 21 days); adding Modification A into the solution to form a mixture at the first temperature; and removing (e.g., evaporating) the organic solvent (e.g., isopropanol) from the mixture after maintaining the mixture (e.g., under shaking) at the first temperature for a second period of time (e.g., at least about 12 hours, at least about 1 day, 2 days, 3 days, or at least about 4 days) to obtain Modification E. In one embodiment, the Modification E obtained is seed material.

In yet another aspect, the invention relates to a process of making Modification E comprising: (a) providing a solution of succinic acid in a first organic solvent (e.g., an alcohol such as 2-propanol) at a second temperature ranging between about 70° C. and about 85° C. (e.g., about 72-78° C., about 73-77° C., about 74-76° C., about 75° C.); (b) providing a solution of free base of ribociclib in a second organic solvent (e.g., an alcohol such as 2-propanol) at a third temperature ranging between about 60° C. and about 85° C. (e.g., about 62-80° C., about 72-78° C., about 73-77° C., about 74-76° C., about 75° C.); (c) transferring the solution of free base of ribociclib (e.g., via pre-heated (e.g., about 75° C.) transfer lines over a pre-heated plate filter, an active carbon filter cartridge and a particle filter) to a crystallization vessel; (d) adding the solution of succinic acid (e.g., transferring over a particle filter) to said crystallization vessel at a fourth temperature ranging between about 60° C. and about 85° C. (e.g., 62-80° C., about 72-78° C., about 73-77° C., about 74-76° C., about 75° C.); (e) immediately after the addition in (d) is complete, adding seed crystals of pure Mod E (e.g., as in a suspension of 2-propanol, with at least 1 mass/% seed crystals related to expected ribociclib succinate yield) to obtain a turbid mixture (e.g., after stirring at medium to high stirrer speed for about 15 minutes); (0 cooling the turbid mixture to a fifth temperature ranging between about 0° C. and about 20° C. (e.g., about 5-15° C. or about 10° C.) to obtain Modification E; (g) optionally separating Modification E from the mixture (by e.g., isolating Modification E via filtration) and optionally rinsing the filtered solid with an organic solvent such as 2-propanol; and (h) optionally drying Modification E obtained from step (g), e.g., at 60° C. jacket temperature and e.g., at ≤20 mbar.

Specific embodiments of the invention will now be demonstrated by reference to the following examples. It should be understood that these examples are disclosed solely by way of illustrating the invention and should not be taken in any way to limit the scope of the present invention.

Example 1 Producing the Seed Material for Modification E

Modification E is extremely difficult to produce in absence of seed material. In order to produce Mod. E the following experiments were performed.

To 3.5 mL of a solution at a concentration ranging from 0.35 to 0.50 mg/mL of ribociclib monosuccinate in dry isopropanol at 60° C., 3 beads of activated molecular sieves 3 Å were added. The resulting mixture was kept for 2 weeks under gentle shaking (e.g., via a vibrating shaker with low frequency. About 10 mg of ribociclib succinate Mod A were added to the reaction mixture and the solution was maintained under shaking for 2 additional days at 60° C. The molecular sieve beads were removed and the solution was gently evaporated until dryness. The resulting powder which consisted of Mod. E and a trace of molecular sieve, as confirmed by XRPD analysis, was used for further experiments, as described below.

Example 2 Production of Mod. E Using Seed Material

Succinic acid was dissolved in 2-propanol at 72-78° C.
Free base of ribociclib was dissolved in 2-propanol at 72-78° C. (The free base typically dissolves above 62° C.). A clear or slightly hazy solution was obtained after stirring for up to 30 minutes.

The solution of free base of ribociclib in 2-propanol was transferred via pre-heated (75° C.) transfer lines over a pre-heated plate filter, an active carbon filter cartridge and a particle filter into the crystallization vessel (75° C. jacket temperature). The transfer line was rinsed with warm 2-propanol.

The solution of succinic acid in 2-propanol was transferred over a period of approximately 60 min. over a particle filter to the ribociclib free base solution in the crystallization vessel at 73-77° C. Immediately after the addition was complete, a suspension of seed crystals of pure Mod E in 2-propanol (minimum of 1 mass/% seed related to expected ribociclib succinate yield) was added. Stirring was continued at medium to high stirrer speed and after approximately 15 minutes, turbidity should be observed. The vessel that contained the succinic acid was rinsed with 2-propanol and the suspension was cooled slowly to 10° C. internal temperature in approximately 20 h.

The product was isolated by filtration over a Nutsche filter and the wet cake was rinsed with 2-propanol. The wet filter cake was then dried at 60° C. jacket temperature and ≤20 mbar.

Example 3 Formation of Ribociclib Succinate Dihydrate, Modification $H_B$

Ribociclib succinate Modification A can be converted into a dihydrate form, Modification $H_B$. This may happen when exposed to a water activity higher than 70% relative humidity (RH). This conversion is observed in bulk at 40° C./75% RH. Transformation is observed in solvent mediated conditions with appropriate water activity.

Modification $H_B$ can also be converted from Modification E. Modification $H_B$ of ribociclib succinate was obtained from suspension equilibration of Modification E of ribociclib succinate at water activities (aH2O) of ≥0.68 at 25° C. It was found in suspension equilibration in mixtures of ethanol and water at 5° C., 25° C., and 50° C. It can be obtained as the main component of the product of suspension equilibration in pure water at 25° C.

Example 4 XRPD

Bruker D8 Advance; LynxEye detector; Cu-Kα radiation; standard measurement conditions: Bragg-Brentano reflection geometry, 40 kV and 40 mA tube power, 0.02° 2θ step size, 37-s step time, 2.5-50° 2θ scanning range. The powder samples were measured in 0.1-mm-deep, silicon single-crystal sample holders. No special treatment was used in preparing the samples other than the application of slight pressure to get a flat surface. An ambient air atmosphere was used for all measurements. All samples were rotated during the measurement.

Example 5 XRPD of Ribociclib Succinate Modification A

Modification A of ribociclib succinate was characterized by XRPD in reflection mode and the diffractogram is presented in FIG. 1.

Table 3 below shows the XRPD peaks for Modification A of ribociclib succinate, measured in reflection mode with a Copper K alpha source

TABLE 3

XRPD peak table for Modification A of ribociclib succinate

| Angle (°2θ) | Intensity (qualitative) |
|---|---|
| 7.6 | high |
| 9.90 | low |
| 14.00 | low |
| 14.5 | medium |
| 15.3 | low |
| 18.0 | low |
| 21.3 | medium |
| 21.6 | medium |
| 27.7 | low |

(High intensity >50%; 50% > Medium > 20%; Low <20%)
The value of each of the 2θ value is accurate within ±0.2

Example 6 XRPD of Ribociclib Succinate Modification E

Figure 2:
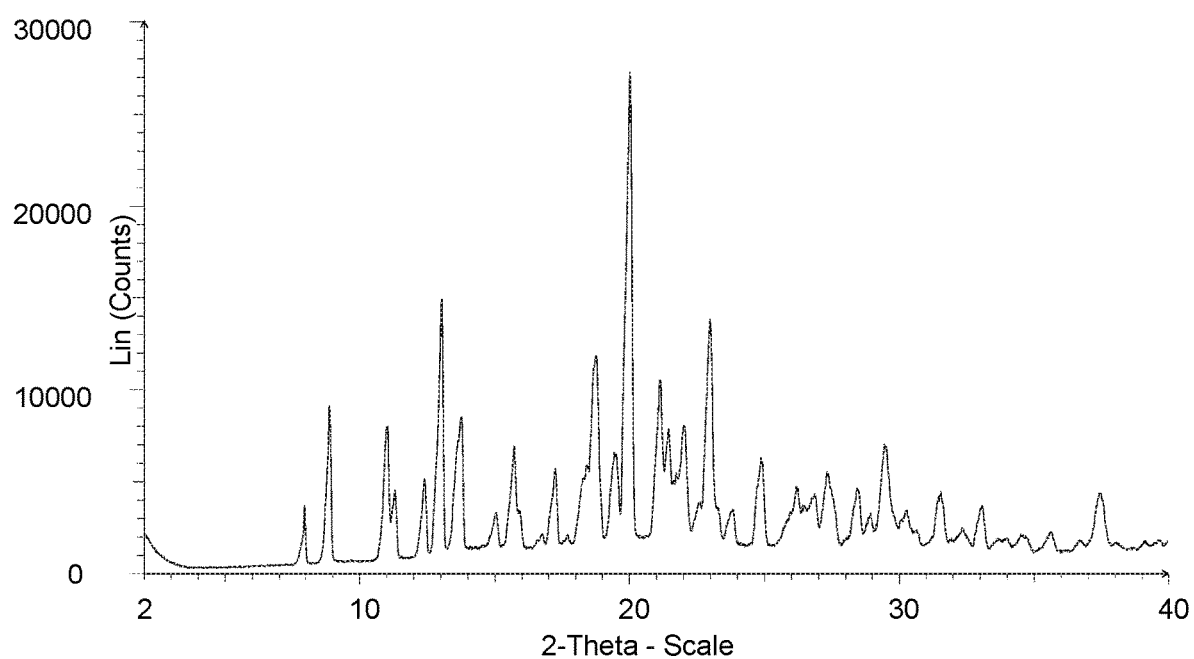
FIG. 2 shows the XRPD diffractogram of anhydrous Modification E of ribociclib succinate recorded in reflection mode.

Modification E of ribociclib succinate was characterized by XRPD in reflection mode (see FIG. 2).

Table 4 below shows the XRPD peaks for anhydrous Modification E of ribociclib succinate, measured in reflection mode with a Copper K alpha source

TABLE 4

XRPD peak table for anhydrous Modification E of ribociclib succinate

| Angle (°2θ) | Intensity (qualitative) |
|---|---|
| 7.9 | low |
| 8.8 | medium |
| 11.0 | medium |
| 12.4 | low |
| 13.0 | high |
| 13.7 | medium |
| 15.7 | medium |
| 17.4 | low |
| 18.7 | medium |
| 20.0 | high |
| 21.1 | medium |
| 23.0 | high |
| 24.9 | medium |

(High intensity >50%; 50% > Medium > 20%; Low <20%)
The value of each of the 2θ value is accurate within ±0.2.

Modification E is characterized by an X-ray powder diffraction pattern with peaks at 11.0°+/−0.2°, 13.0°+/−0.2°, and 17.2°+/−0.2° (CuKα λ=1.5406 Å). Modification E is further characterized by a powder x-ray diffraction pattern comprising four or more 2θ values (CuKα λ=1.5406 Å) selected from the group consisting of 11.0°+/−0.2°, 13.0°+/−0.2°, 17.2°+/−0.2°, 20.0°+/−0.2°, and 23.0°+/−0.2°, at a temperature of about 22° C. Modification E is further characterized by a powder x-ray diffraction pattern comprising five or more 2θ values (CuKα λ=1.5406 Å) selected from the group consisting of 8.8°+/−0.2°, 11.0°+/−0.2°, 13.0°+/−0.2°, 13.7°+/−0.2°, 15.7°+/−0.2°, 17.2°+/−0.2°, 18.7°+/−0.2°, 20.0°+/−0.2°, 21.1°+/−0.2°, 23.0°+/−0.2°, and 24.9°+/−0.2°, at a temperature of about 22° C. Modification E is further characterized by a powder x-ray diffraction pattern comprising six or more 2θ values (CuKα λ=1.5406 Å) selected from the group consisting of 7.9°+/−0.2°, 8.8°+/−0.2°, 11.0°+/−0.2°, 12.4°+/−0.2°, 13.0°+/−0.2°, 13.7°+/−0.2°, 15.7°+/−0.2°, 17.2°+/−0.2°, 18.7°+/−0.2°, 20.0°+/−0.2°, 21.1°+/−0.2°, 23.0°+/−0.2°, and 24.9°+/−0.2°, at a temperature of about 22° C.

Example 7 XRPD of Ribociclib Hemisuccinate Modification F

Figure 3:
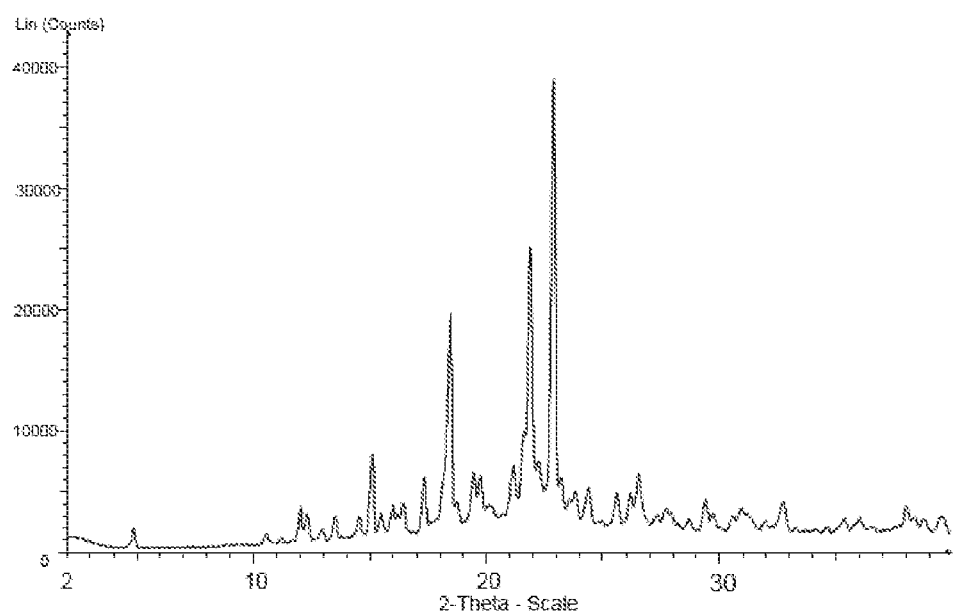
FIG. 3 shows the XRPD diffractogram of anhydrous Modification F of ribociclib succinate recorded in reflection mode.

Modification F of ribociclib succinate was characterized by XRPD in reflection mode (see FIG. 3).

Table 5 below shows the XRPD peaks for anhydrous Modification F of ribociclib hemisuccinate, measured in reflection mode with a Copper K alpha source

TABLE 5

XRPD peak table for anhydrous Modification
F of ribociclib hemisuccinate

| Angle (°2θ) | Intensity (qualitative) |
|---|---|
| 4.9 | low |
| 11.9 | Low |
| 12.6 | Low |
| 15.0 | Low |
| 18.4 | Medium |
| 21.8 | Medium |
| 22.8 | high |
| 26.6 | Low |
| 29.4 | low |
| 32.7 | low |

(High intensity >50%; 50% > Medium > 20%; Low <20%)
The value of each of the 2θ value is accurate within ±0.2.

Modification F is characterized by an X-ray powder diffraction pattern with peaks at 4.9°+/−0.2°, 11.9°+/−0.2°, and 12.6°+/−0.2° (CuKα λ=1.5406 Å). Modification F is further characterized by a powder x-ray diffraction pattern comprising four or more 2θ values (CuKα λ=1.5406 Å) selected from the group consisting of 4.9°+/−0.2°, 11.9°+/−0.2°, 12.6°+/−0.2° and 22.8°+/−0.2°, at a temperature of about 22° C. Modification F is further characterized by a powder x-ray diffraction pattern comprising five or more 2θ values (CuKα λ=0.5406 Å) selected from the group consisting of 4.9°+/−0.2°, 11.9°+/−0.2°, 12.6°+/−0.2°, 22.8°+/−0.2° and 26.6°+/−0.2°, at a temperature of about 22° C. Modification F is further characterized by a powder x-ray diffraction pattern comprising six or more 2θ values (CuKα λ=1.5406 Å) selected from the group consisting of 4.9°+/−0.2°, 11.9°+/−0.2°, 12.6°+/−0.2°, 22.8°+/−0.2°, 26.6°+/−0.2° and 29.4°+/−0.2°, at a temperature of about 22° C.

Example 8 XRPD and KF of Ribociclib Succinate Modification $H_B$

Figure 4:
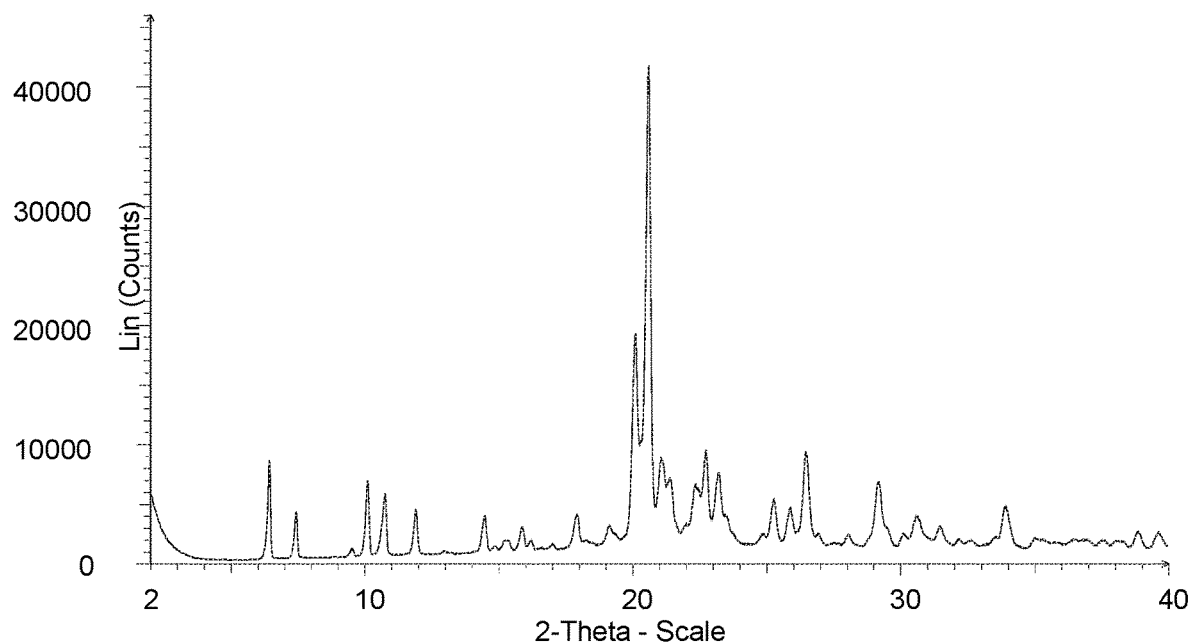
FIG. 4 shows the XRPD diffractogram of the Modification $H_B$ of ribociclib succinate.

Modification $H_B$ of ribociclib succinate was characterized by XRPD and shown in FIG. 4.

Table 6 below shows the XRPD peaks for Modification $H_B$ of ribociclib succinate, measured in reflection mode with a Copper K alpha source.

TABLE 6

XRPD peak table for Modification $H_B$ of LEE011 succinate

| Angle (°2θ) | Intensity (qualitative) |
|---|---|
| 6.4 | medium |
| 7.4 | low |
| 10.1 | low |
| 10.7 | low |
| 11.9 | low |
| 20.1 | medium |
| 20.6 | high |
| 22.7 | medium |
| 26.5 | medium |
| 33.9 | low |

(High intensity >50%; 50% > Medium > 20%; Low <20%)
The value of each of the 2θ value is accurate within ±0.2.

The frequent appearance of this form under aqueous conditions led to the hypothesis that it might be a hydrated form. A monohydrate of ribociclib succinate would theoretically contain 3.2 wt.-% $H_2O$, a sesquihydrate 4.7 wt.-%, and a dihydrate 6.1 wt.-%. Karl-Fischer titration of Modification $H_B$ of ribociclib succinate reveals a water content of 6.1 wt.-%, which is consistent with Modification $H_B$ being a monosuccinate dihydrate.

Example 9 XRPD of Ribociclib Hemisuccinate Hydrate Modification $H_A$

Modification $H_A$ of the hemisuccinate hydrate of ribociclib was characterized by XRPD in reflection mode with a Copper K alpha source. The diffractogram is presented in FIG. 5.

TABLE 7

XRPD peak table for Modification $H_A$ of the ribociclib hemisuccinate

| Angle (°2θ) | Intensity (qualitative) |
|---|---|
| 4.7 | low |
| 8.9 | low |
| 10.7 | medium |
| 13.0 | high |
| 16.2 | medium |
| 17.9 | medium |
| 18.5 | high |
| 20.0 | high |
| 21.6 | high |
| 22.1 | high |
| 26.2 | medium |
| 28.8 | medium |

(High intensity >50%; 50% > Medium > 20%; Low <20%)
The value of each of the 2θ value is accurate within ±0.2.

Example 10 Differential Scanning Calorimetry (DSC)

DSC studies were conducted at the following settings.

| | |
|---|---|
| Instrument | Perkin Elmer Diamond, Mettler DSC1or DSC822e, or TA instrument DSC Q2000 |
| Temperature range | 30-300° C. |
| Scan rate | If not specified 20 K/min |
| Nitrogen flow | Instrument specific |

Example 11 DSC Study of Ribociclib Succinate Mod A

DSC curves of ribociclib succinate Modification A are strongly affected by the heating rate in relation to decomposition. Since the thermal event is related to melting/decomposition, the related enthalpy value is reported for information only. See Table 8.

Modification A shows melting followed by decomposition at about 205° C., when heated in a DSC at 10K/min.

Figure 6:
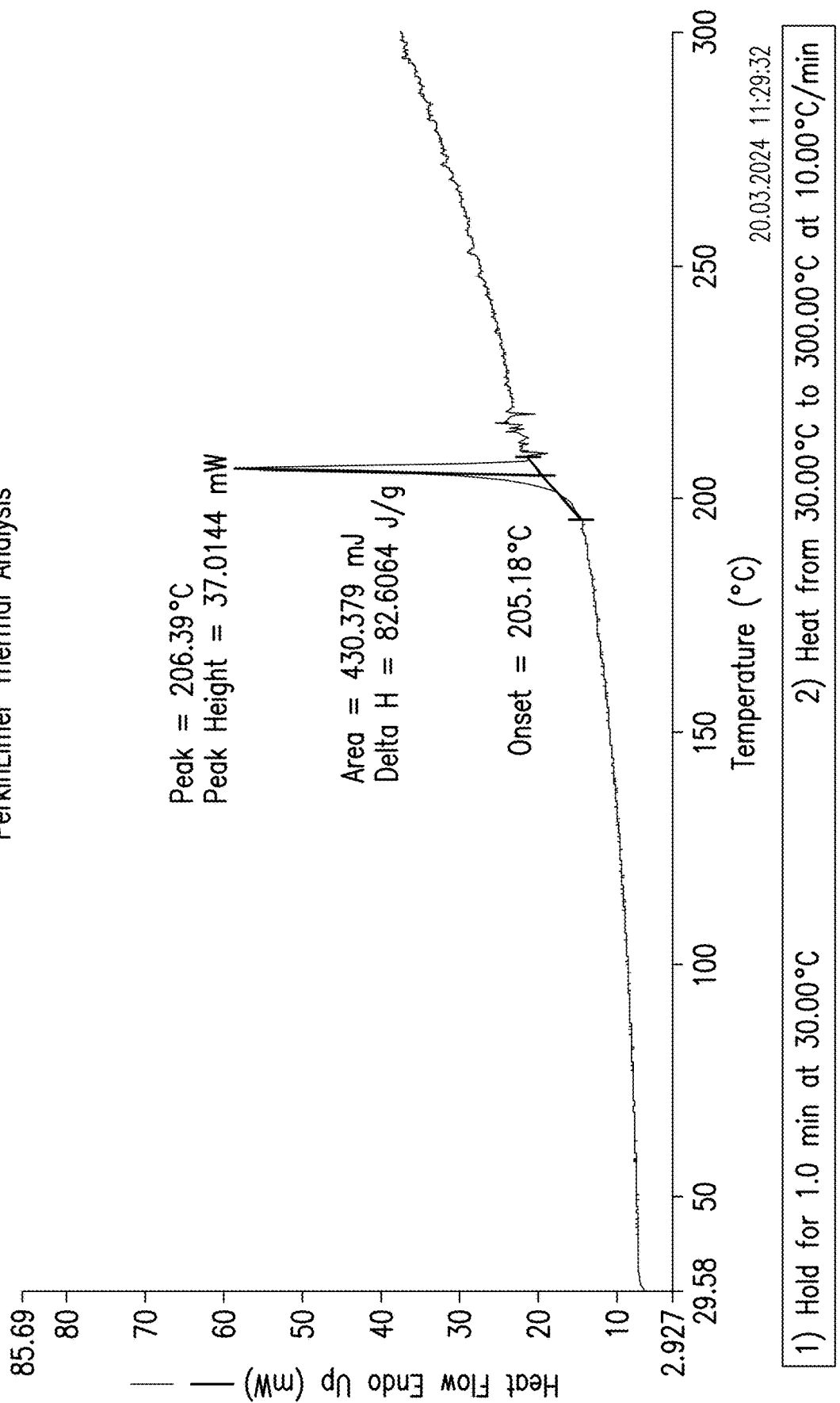
FIG. 6 shows the DSC (differential scanning calorimetry) trace of ribociclib succinate Modification A.

FIG. 6 shows the DSC plot of ribociclib succinate Modification A at a heating rate of 10 degrees Celsius per minute.

TABLE 8

Melting onset of ribociclib succinate Modification A

| Heating rate (in ° C./min) | Endothermic onset (in ° C.) | Enthalpy (J/g) |
|---|---|---|
| 10 (with pinhole) | 205.2 | 82.6 |

Example 12 DSC Study of Ribociclib Succinate Mod E

DSC curves of ribociclib succinate Modification E are strongly affected by the heating rate in relation to decomposition. Since the thermal event is related to melting/decomposition, the related enthalpy value is reported for information only. See Table 9.

Figure 7:
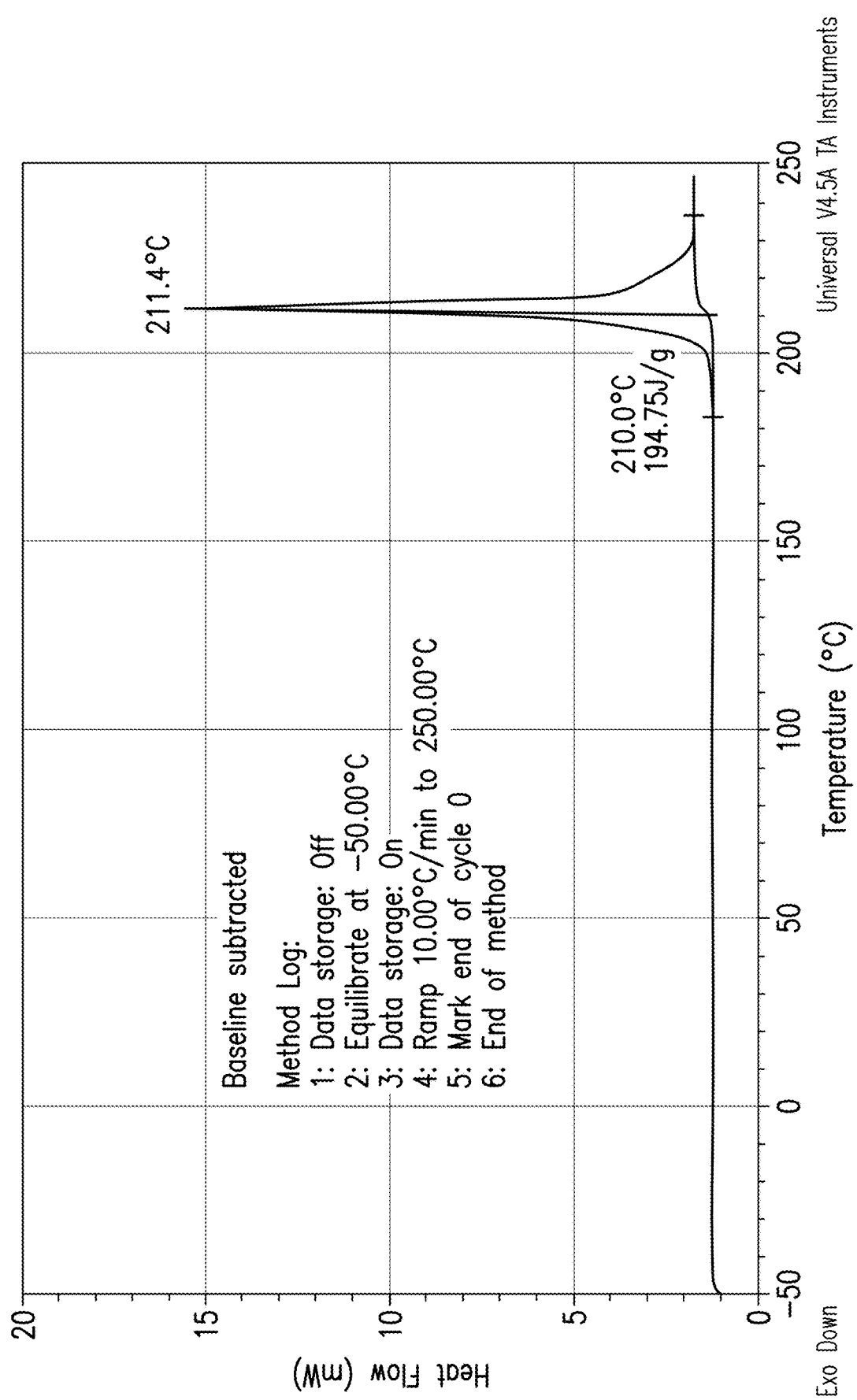
FIG. 7 shows the DSC trace of anhydrous ribociclib succinate Modification E.

FIG. 7 shows the DSC plot of ribociclib succinate Modification E at a heating rate of 10 degrees Celsius per minute.

TABLE 9

Melting onset of ribociclib succinate Modification E

| Heating rate (in °C./min) | Endothermic onset (in °C.) | Enthalpy (J/g) and comments |
|---|---|---|
| 10 (with pinhole) | 210.0 | 194.8 |

Example 13 DSC Study of Ribociclib Succinate Modification F

DSC curves of ribociclib succinate Modification F is strongly affected by the heating rate in relation to decomposition. Since the thermal event is related to melting/decomposition, the related enthalpy value is reported for information only. See Table 10.

Figure 8:
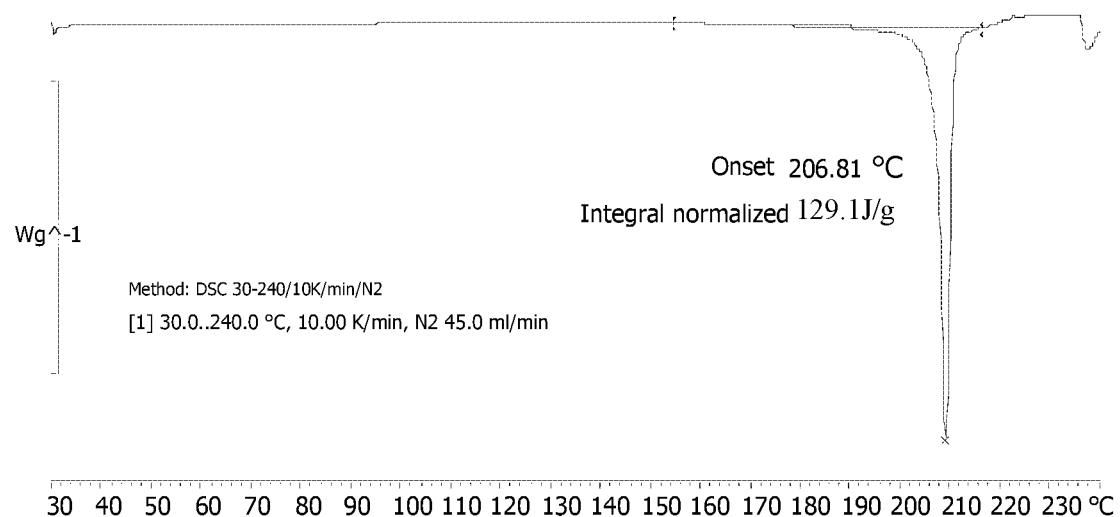
FIG. 8 shows the DSC trace of anhydrous ribociclib succinate Modification F.

FIG. 8 shows the DSC plot of ribociclib succinate Modification F at a heating rate of 10 degrees Celsius per minute.

TABLE 10

Melting onset of ribociclib succinate Modification F

| Heating rate (in °C./min) | Endothermic onset (in °C.) | Enthalpy (J/g) and comments |
|---|---|---|
| 10 (with pinhole) | 206.8 | 129.1 |

Example 14 DSC Study of Ribociclib Succinate Modification $H_B$

The DSC curves of ribociclib succinate dihydrate, Modification $H_B$, are very complex. The first events are likely related to the loss of the water molecules that occurs in two steps, in good agreement with thermogravimetric analysis. These events are likely dependent on kinetic conditions. Other thermal events are difficult to interpret.

Comparing the standard DSC data obtained in Al-crucibles with data from a sealed gold crucible, ribociclib succinate $H_B$ is melting at about 155° C. Melting is again followed by decomposition.

The resulting phase after dehydration could not be assigned, because dependence of melting event as function of heating rate and typical melting decomposition of ribociclib succinate related phases.

Figure 9:
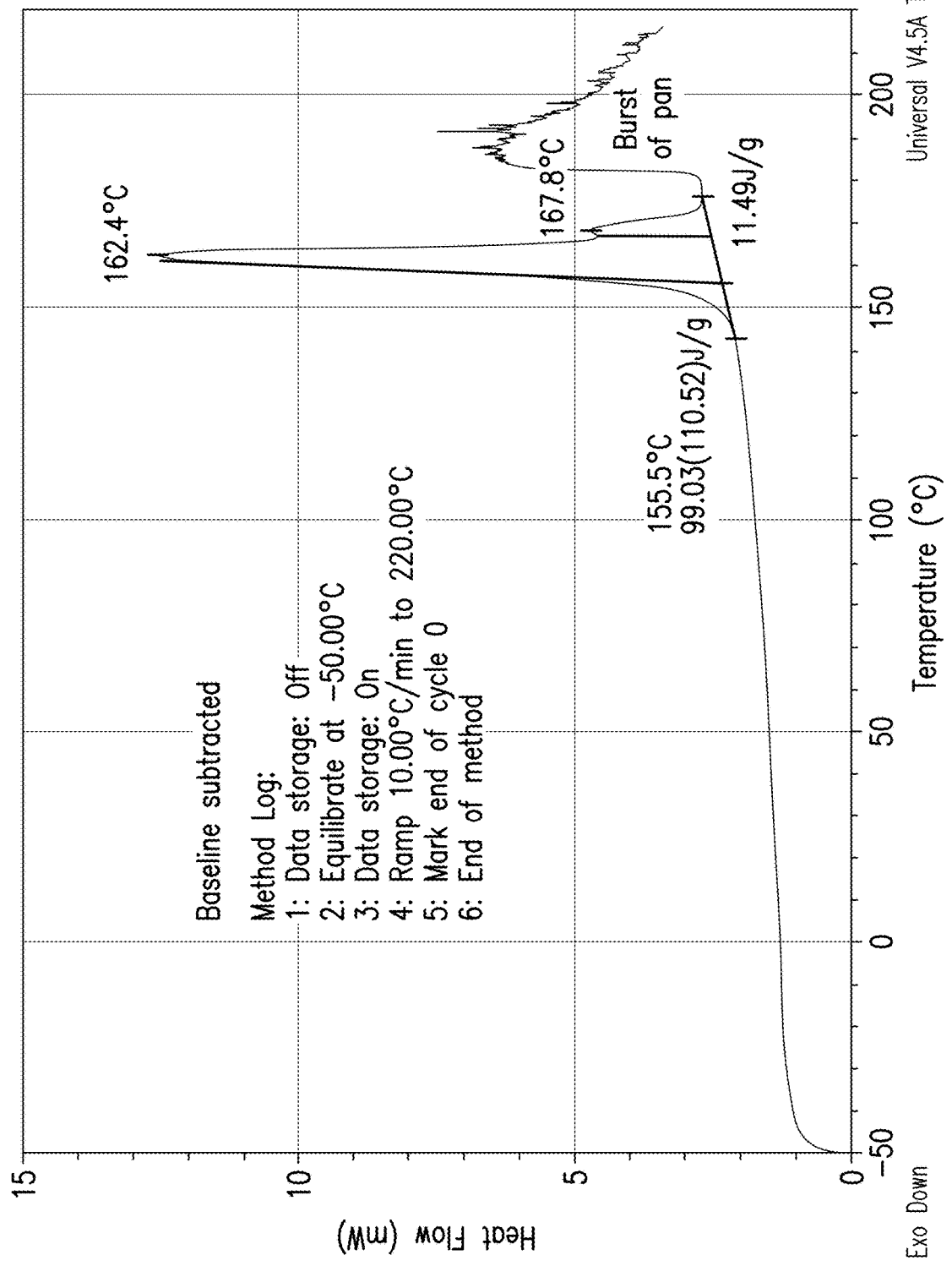
FIG. 9 shows the DSC plot of ribociclib succinate dihydrate, Modification $H_B$ at heating rate of 10 degrees Celsius per minute, in closed gold crucible.

FIG. 9 shows DSC plot of ribociclib succinate dihydrate, Modification $H_B$ at heating rate of 10 degrees Celsius per minute, closed gold crucible.

TABLE 11

Thermal behavior of ribociclib succinate dihydrate, Modification $H_B$

| Heating rate (in °C./min) | Endothermic onset (in °C.) | Enthalpy (J/g) and comments |
|---|---|---|
| 10 (closed, gold) | 155.5 | 110.5 |

Example 15 Thermogravimetry of Modification A

In good accordance with DSC study, ribociclib succinate Modification A undergoes to decomposition at about 200° C. From 30 to 180° C., the loss on drying value is less than 0.05%, followed by decomposition.

Figure 10:
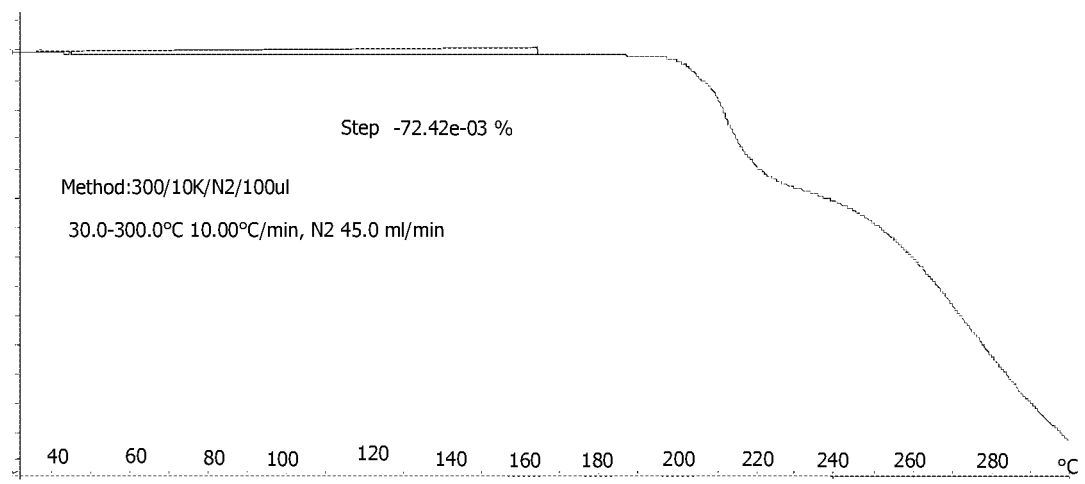
FIG. 10 shows the thermogravimetric curve of ribociclib succinate Modification A.

FIG. 10 shows the thermogravimetric curve of Modification A at heating rate at 10 degrees Celsius per minute.

Example 16 Thermogravimetry of Modification E

In good agreement with the DSC study, ribociclib succinate Modification E undergoes to decomposition at about 200° C. From 30 to 180° C., the loss on drying value is less than 0.05%.

Figure 11:
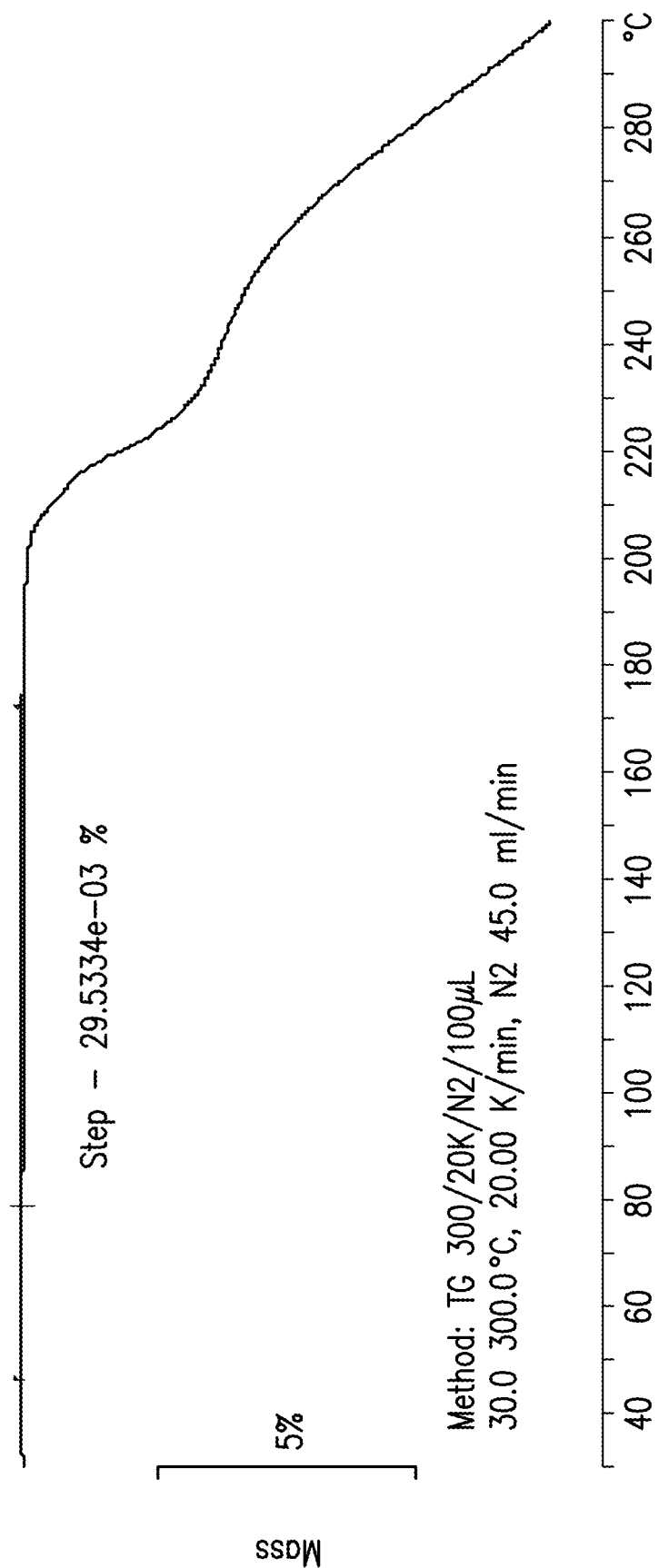
FIG. 11 shows the thermogravimetric curve of anhydrous ribociclib succinate Modification E.

FIG. 11 shows the thermogravimetric curve of Modification E at heating rate at 10 degrees Celsius per minute.

Example 17 Thermogravimetry of Modification F

In good agreement with the DSC study, ribociclib succinate Modification F undergoes to decomposition at about 0.9° C. From 30 to 140° C., the loss on drying value is less than 0.0%.

Figure 12:
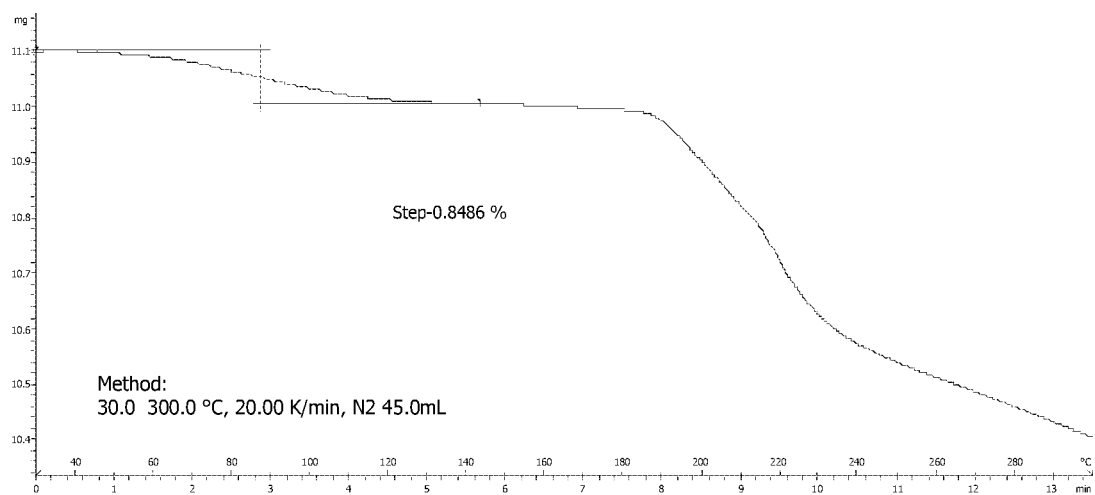
FIG. 12 shows the thermogravimetric curve of anhydrous ribociclib succinate Modification F.

FIG. 12 shows the thermogravimetric curve of Modification F at heating rate at 10 degrees Celsius per minute.

Example 18 Thermogravimetry of Modification $H_B$

In good agreement with the DSC study, ribociclib succinate dihydrate, Modification $H_B$ underwent loss of water at about 120° C. corresponding to a mass loss of about 5.8%. This mass loss was found to be coherent with water determined by Karl Fischer (6.1%). At about 200° C. the material also decomposes.

Figure 13:
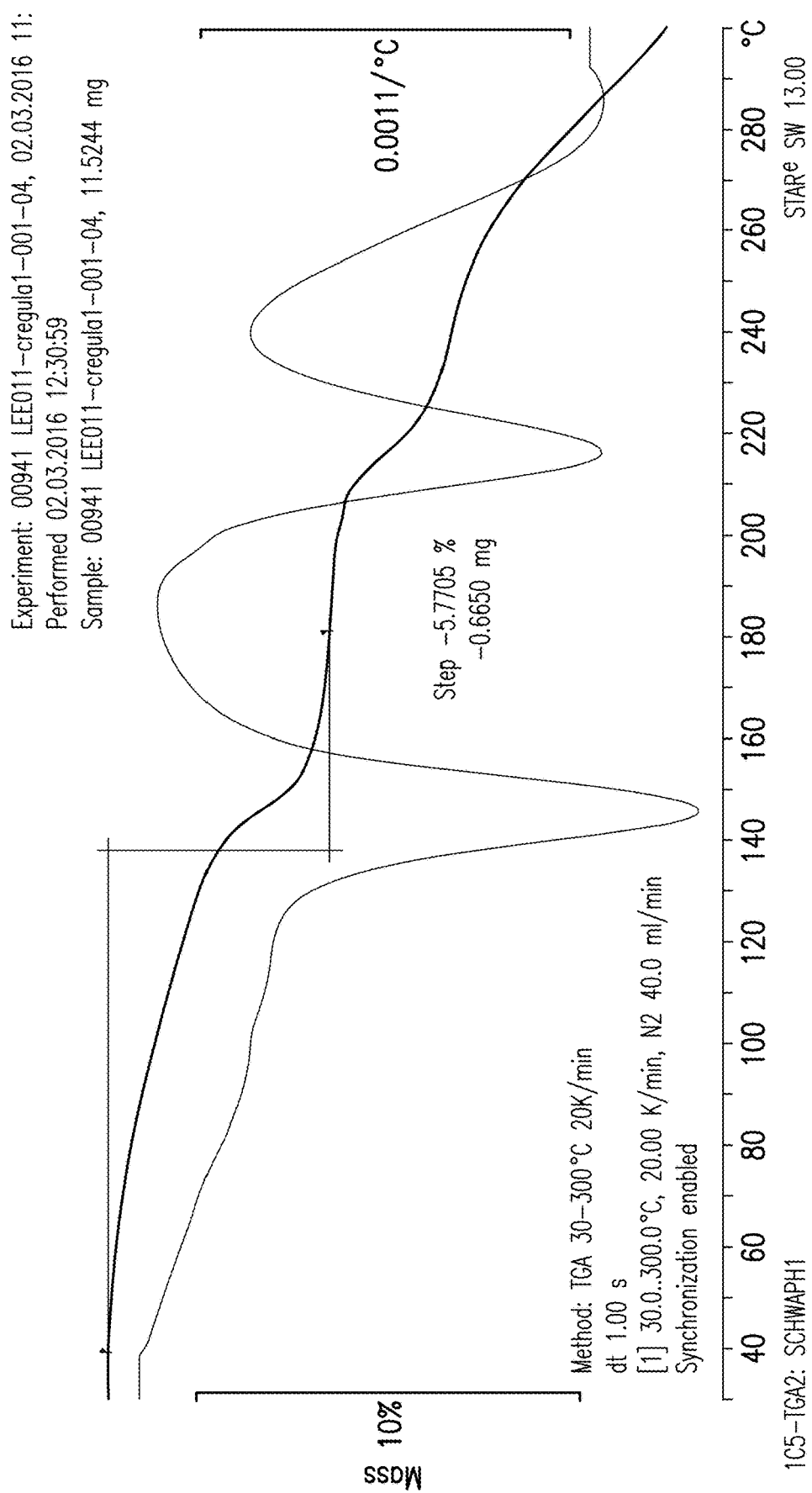
FIG. 13 shows the thermogravimetric curve of Modification $H_B$ at heating rate at 10 degrees Celsius per minute.

FIG. 13 shows the thermogravimetric curve of Modification $H_B$ at heating rate at 10 degrees Celsius per minute.

Example 19 Hygroscopicity Studies

A. Sorption/Desorption Isotherms: Anhydrous Modification of Mod a and Mod E

Anhydrous modifications A and E of ribociclib succinate were submitted to DVS analysis.

Figure 14:
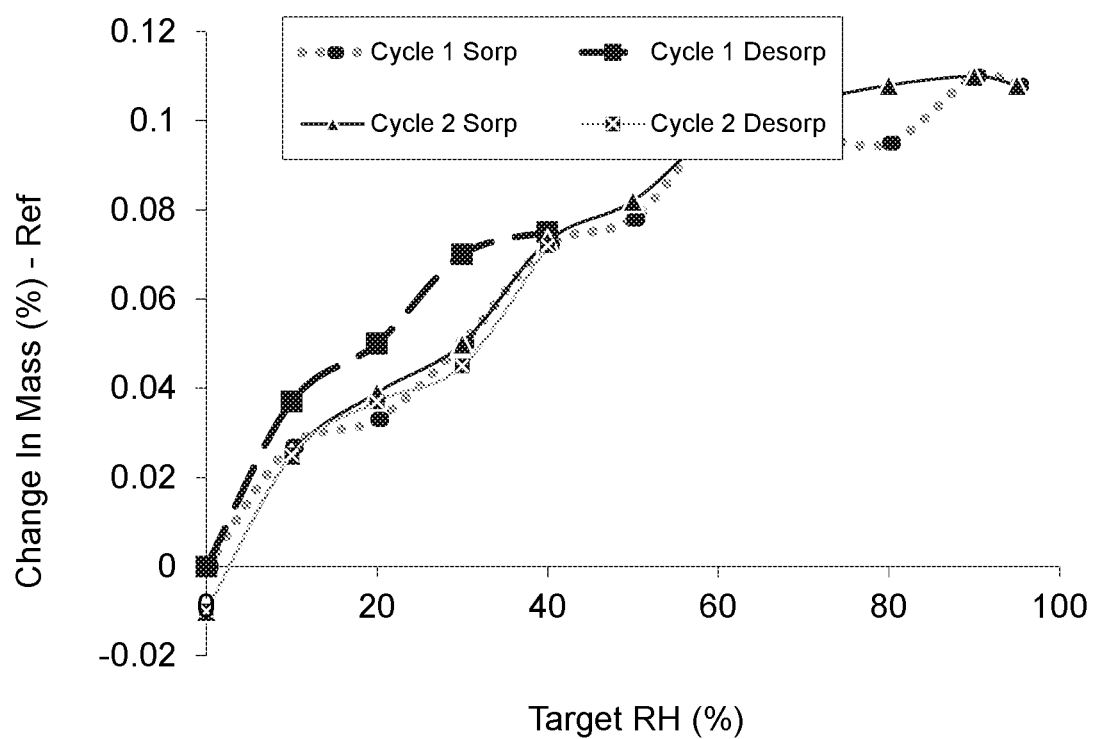
FIG. 14 shows the DVS (dynamic vapor sorption) isotherm of ribociclib succinate Modification A at 25 degrees Celsius.
Figure 15:
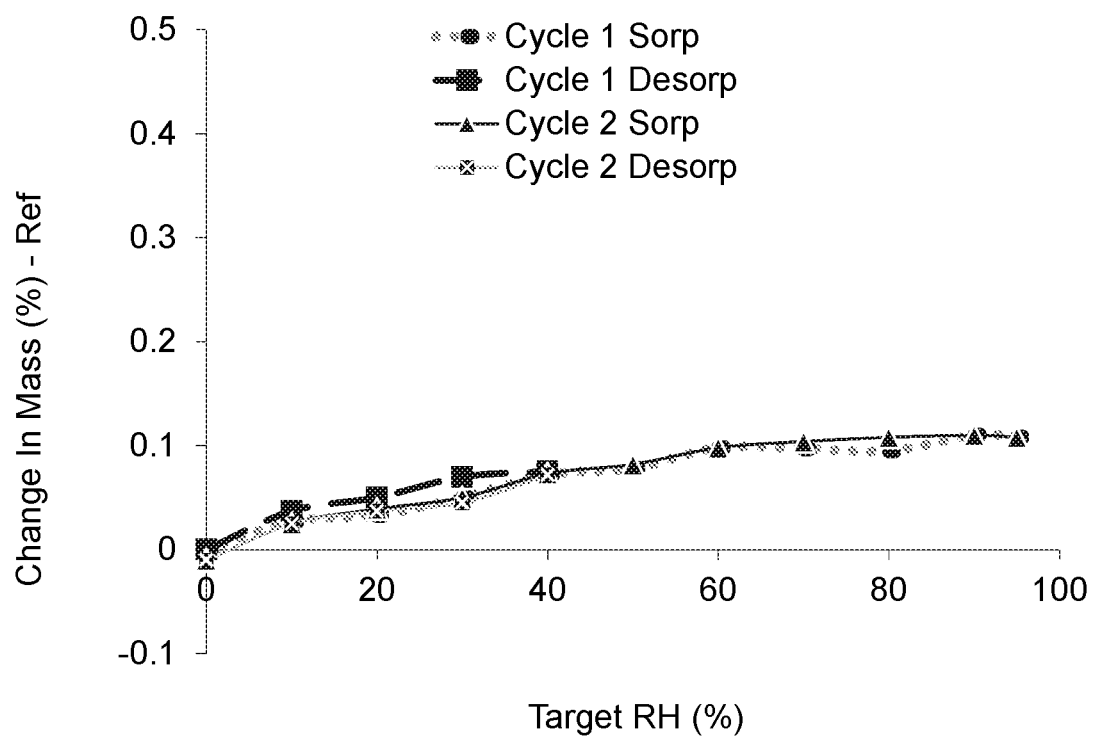
FIG. 15 shows the DVS isotherm of anhydrous ribociclib succinate Modification E at 25 degrees Celsius.

The results are reported in FIGS. 14 and 15 and in Table 12.

FIG. 14 shows DVS isotherm of ribociclib succinate Modification A at 25 degrees Celsius.

FIG. 15 shows DVS isotherm of ribociclib succinate Modification E at 25 degrees Celsius.

TABLE 12

DVS test on polymorphs of ribociclib succinate anhydrous modification

| Relative humidity [%] | Modification A | | Modification E | |
|---|---|---|---|---|
| | Sorption [wt %] | Desorption [wt %] | Sorption [wt %] | Desorption [wt %] |
| 0 | 0.0 | 0.0 | 0.0 | 0.0 |
| 10 | 0.1 | 0.1 | 0.0 | 0.0 |
| 20 | 0.1 | 0.1 | 0.0 | 0.1 |
| 30 | 0.2 | 0.1 | 0.1 | 0.1 |
| 40 | 0.2 | 0.1 | 0.1 | 0.1 |
| 50 | 0.2 | | 0.1 | |
| 60 | 0.2 | | 0.1 | |
| 70 | 0.3 | | 0.1 | |
| 80 | 0.3 | | 0.1 | |
| 90 | 0.5 | | 0.1 | |
| 95 | 0.7 | | 0.1 | |
| XRPD after DVS | No change | | No change | |

As shown above, ribociclib succinate Modification A takes up about 0.7% water in comparison to the dry state (when exposed to 0% RH) when exposed to 95% RH in DVS cycle at 25° C., whereas ribociclib succinate Modification E has a lower mass change (max water uptake of 0.1%).

The data set shows that ribociclib succinate Modification A can be classified as slightly hygroscopic since maximum mass change, when exposed to 92% HR. and compared to the dry state is about 0.7% at 25° C.

In contrast, Modification E is classified as not hygroscopic.

B. Sorption/Desorption Isotherms: Ribociclib Succinate Dehydrate $H_B$

TABLE 13

DVS test of ribociclib succinate dihydrate $H_B$ at 25 degrees Celsius

| Relative humidity [%] | Modification $H_B$ | |
|---|---|---|
| | Sorption [wt %] | Desorption [wt %] |
| 0 | 0.0 | 0.0 |
| 10 | 0.8 | 1.2 |
| 20 | 1.3 | 1.7 |
| 30 | 1.7 | 1.9 |
| 40 | 1.9 | 2.0 |
| 50 | 2.1 | |
| 60 | 2.2 | |
| 70 | 2.3 | |
| 80 | 2.4 | |
| 90 | 2.5 | |
| 95 | 2.5 | |
| XRPD after DVS | No change | |

Note:
upon exposure to 0% RH equilibrium was not reached.

Figure 16:
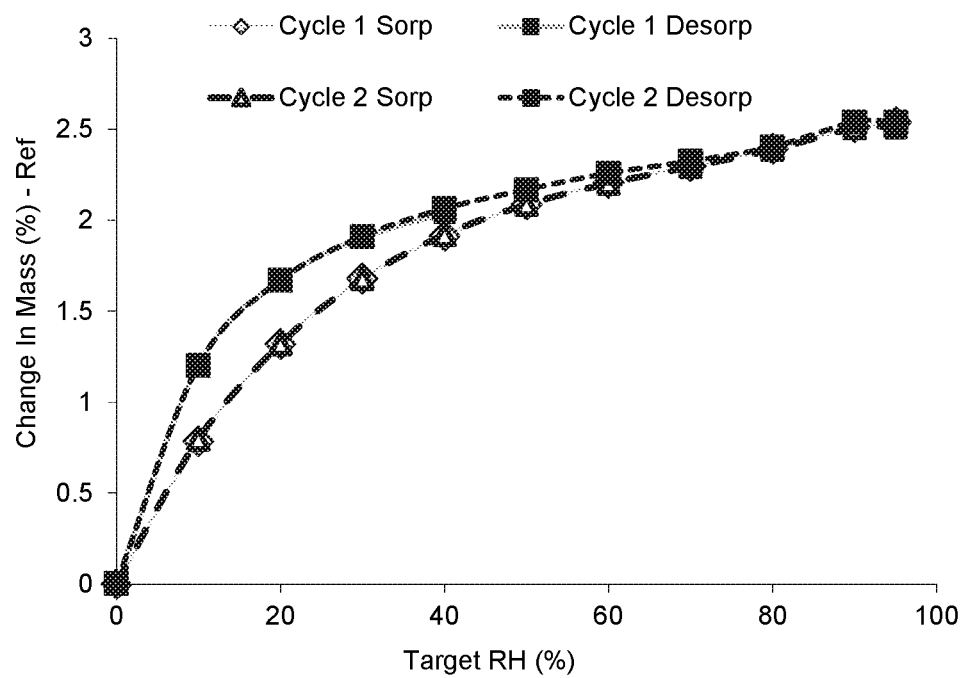
FIG. 16 depicts the DVS isotherm of ribociclib succinate dihydrate $H_B$ at 25 degrees Celsius.

FIG. 16 depicts the DVS isotherm of ribociclib succinate dihydrate $H_B$ at 25 degrees Celsius.

C. Study of Hydrate Formation i. Exposure at Ambient Temperature at Various Relative Humidity for 1 Day

Aliquots from ribociclib succinate Modification A were exposed in a desiccator with saturated solution of inorganic salt or drying agent to provide a range of various relative humidities.

Ribociclib succinate Modification A is physically stable when exposed up to 80% RH at ambient temperature for 1 day. When exposed to 92% RH for 1 day, some additional peaks at about 4.7, 6.4, 12.0 and 13.0 degree 2θ can be detected. These peaks can be assigned to ribociclib hemisuccinate Modification $H_A$.

Differences in terms of peak shape and peak relative intensities are due to texture effects and sample preparation.

ii. Exposure at Ambient Temperature at Various Relative Humidity for 10 Days A similar behavior is observed after 10 days, but complete conversion is achieved when exposed to 92% RH. The material shows poor crystallinity and loss on drying by thermogravimetry was assessed to 3.9% in contrast to the starting material with a value lower than 0.05%.

It was found that upon exposure for a sufficient amount of time at a relative humidity close or higher than 92%, ribociclib succinate Modification A starts to deliquesce. If this deliquescent material (corresponding to a highly concentrated solution of ribociclib succinate) is dried, for instance by exposure to a lower relative humidity, it can recrystallize into this other crystalline form. This crystalline form was further identified as Modification $H_A$. Further characterization of this form $H_A$ confirmed that it refers to a hydrated form of the hemisuccinate salt of ribociclib with a ratio ribociclib:succinic acid:water 2:1:1. It seems that the water content in this phase may vary (e.g., not exactly with a ratio of ribociclib:succinic acid:water being 2:1:1), depending on sample preparation, but the XRPD pattern of Mod. $H_A$ remains substantially the same as that in FIG. 5.

D. Long Term Exposure of Mod A to High Relative Humidity

During long term stability studies of various batches exposed at 75% RH at various temperature and less protective packaging material, ribociclib succinate Modification A was physically unstable at 40 or 50° C. leading to the appearance of additional diffraction peaks when analyzed by XRPD.

What is claimed is:

1. A process of making ribociclib succinate crystalline form Modification E comprising:
   providing a solution of about 0.1 mg/mL to about 1.0 mg/mL ribociclib monosuccinate in an organic solvent wherein the solution is substantively free of water and maintained at a first temperature ranging between about 50° C. and about 80° C. for a first period of time;
   mixing ribociclib succinate crystalline form Modification A with the solution to form a mixture at the first temperature; and
   removing the organic solvent from the mixture after maintaining the mixture at the first temperature for a second period of time to obtain Modification E;
   wherein modification E exhibits an X-ray powder diffraction pattern substantially in accordance with FIG. 2, and modification A exhibits an X-ray powder diffraction pattern substantially in accordance with FIG. 1.

* * * * *